United States Patent
Kuno et al.

(10) Patent No.: US 10,428,310 B2
(45) Date of Patent: Oct. 1, 2019

(54) METHODS AND COMPOSITIONS FOR GENERATING OR MAINTAINING PLURIPOTENT CELLS

(71) Applicant: Regeneron Pharmaceuticals, Inc., Tarrytown, NY (US)

(72) Inventors: Junko Kuno, Holmes, NY (US); Wojtek Auerbach, Ridgewood, NJ (US); David M. Valenzuela, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 39 days.

(21) Appl. No.: 14/884,293

(22) Filed: Oct. 15, 2015

(65) Prior Publication Data

US 2016/0108369 A1  Apr. 21, 2016

Related U.S. Application Data

(60) Provisional application No. 62/064,384, filed on Oct. 15, 2014.

(51) Int. Cl.
*C12N 5/074* (2010.01)

(52) U.S. Cl.
CPC ........ *C12N 5/0696* (2013.01); *C12N 2500/32* (2013.01); *C12N 2500/38* (2013.01); *C12N 2500/44* (2013.01); *C12N 2500/60* (2013.01); *C12N 2501/235* (2013.01); *C12N 2501/727* (2013.01); *C12N 2509/00* (2013.01)

(58) Field of Classification Search
CPC .............. C12N 5/0696; C12N 2500/32; C12N 2500/38; C12N 2500/44; C12N 2500/60; C12N 2501/235; C12N 2501/727; C12N 2509/00

See application file for complete search history.

(56) References Cited

U.S. PATENT DOCUMENTS

| | | | |
|---|---|---|---|
| 6,566,579 B1 | 5/2003 | Jaisser et al. | |
| 8,697,359 B1 | 4/2014 | Zhang | |
| 9,149,026 B2 | 10/2015 | Auerbach et al. | |
| 9,228,208 B2 | 1/2016 | Frendewey et al. | |
| 9,398,762 B2 | 7/2016 | Auerbach et al. | |
| 2003/0175968 A1 | 9/2003 | Golic et al. | |
| 2004/0018626 A1 | 1/2004 | Murphy et al. | |
| 2005/0216966 A1 | 9/2005 | Nagao | |
| 2007/0155013 A1 | 7/2007 | Akaike et al. | |
| 2007/0245424 A1 | 10/2007 | Nagao et al. | |
| 2008/0113437 A1 | 5/2008 | Joly et al. | |
| 2008/0124801 A1 | 5/2008 | Mee et al. | |
| 2008/0299580 A1 | 12/2008 | DeKelver et al. | |
| 2011/0307968 A1 | 12/2011 | Auerbach et al. | |
| 2014/0315301 A1 | 10/2014 | Hanna et al. | |
| 2014/0342458 A1 | 11/2014 | Mali et al. | |
| 2015/0031132 A1 | 1/2015 | Church et al. | |
| 2015/0031133 A1 | 1/2015 | Church et al. | |
| 2015/0067901 A1 | 3/2015 | Auerbach et al. | |
| 2015/0140664 A1 | 5/2015 | Byrne et al. | |
| 2015/0159174 A1 | 6/2015 | Frendewey et al. | |
| 2015/0159175 A1 | 6/2015 | Frendewey et al. | |
| 2015/0240263 A1 | 8/2015 | Holmes et al. | |
| 2015/0376650 A1 | 12/2015 | Auerbach et al. | |
| 2015/0376651 A1 | 12/2015 | Frendewey et al. | |
| 2016/0017301 A1 | 1/2016 | Khalili et al. | |
| 2016/0046960 A1 | 2/2016 | Frendewey et al. | |
| 2016/0060657 A1 | 3/2016 | Frendewey et al. | |
| 2016/0145646 A1 | 5/2016 | Frendewey et al. | |
| 2016/0151491 A1 | 6/2016 | Rabinovich et al. | |
| 2016/0153004 A1 | 6/2016 | Zhang et al. | |
| 2016/0153005 A1 | 6/2016 | Zhang et al. | |
| 2016/0153006 A1 | 6/2016 | Zhang et al. | |
| 2016/0160210 A1 | 6/2016 | Mali et al. | |
| 2016/0175462 A1 | 6/2016 | Zhang et al. | |
| 2016/0177339 A1 | 6/2016 | Voronina et al. | |
| 2016/0184362 A1 | 6/2016 | Duchateau et al. | |
| 2016/0186213 A1 | 6/2016 | Zhang et al. | |
| 2016/0208319 A1 | 7/2016 | Berman et al. | |
| 2016/0264995 A1 | 9/2016 | Yamamoto et al. | |

FOREIGN PATENT DOCUMENTS

| | | | | |
|---|---|---|---|---|
| EP | 1516924 A1 | 3/2005 | | |
| EP | 2457995 A1 * | 5/2012 | ........... | C12N 5/0606 |
| EP | 3009511 A2 | 4/2016 | | |
| WO | WO 2003/087341 A2 | 10/2003 | | |
| WO | WO 2006/044962 A1 | 4/2006 | | |
| WO | WO 2007/117410 A2 | 10/2007 | | |

(Continued)

OTHER PUBLICATIONS

Takahashi et al., Cell, 131: 12-12, Nov. 30, 2007.*
Thomson, Science, 282: 1145-1147, 1998.*
Reubinoff et al. 2000, Nature Biotechnology, vol. 18, pp. 399-404.*
Reijo et al. 2009, Differentiation, vol. 78, pp. 18-23.*
Remarks of Dr. Lyle Armstrong to the UK House of Parliaments' Select Committee on Science and Technology, Fifth Report of Session 2006-07, vol. II, pp. 76-77, Apr. 5, 2007.*
Lai et al., Proc Natl Acad Sci U S A. Mar. 5, 2012; 109(10):3772-7.*
Dominiguez-Bendala et al., Handbook of Stem Cells, Chapter 70: Islet Cell Therapy and Pancreatic Stem Cells, pp. 835-853, 2013.*
Invitrogen, "Two Independent studies demonstrate improved growth characteristic for hESCs in DMEM/F-12 low osmolality medium", pp. 1-2, accessed online https://www.thermofisher.com/order/catalog/product/12660012?ICID=search-product on Jun. 19, 2017, published 2006.*

(Continued)

*Primary Examiner* — Thaian N Ton
(74) *Attorney, Agent, or Firm* — Yonglin Choi; Alston & Bird, LLP

(57) ABSTRACT

Methods and compositions are provided for generating or maintaining human iPS cells in culture. Methods include the use of a low osmolality medium to make human iPS cells, or use of a low osmolality medium to maintain human iPS cells. Methods for making targeted genetic modification to human iPS cells cultured in low osmolality medium are also included. Compositions include human iPS cells cultured and maintained using the low osmolality medium defined herein.

23 Claims, 7 Drawing Sheets

Specification includes a Sequence Listing.

(56) References Cited

FOREIGN PATENT DOCUMENTS

| WO | WO 2011/044684 A1 | 4/2011 |
|---|---|---|
| WO | WO 2011/078665 A1 | 6/2011 |
| WO | WO 2011/156723 A1 | 12/2011 |
| WO | WO 2012/129198 A1 | 9/2012 |
| WO | WO 2013/169802 A1 | 11/2013 |
| WO | WO 2014/099744 A1 | 6/2014 |
| WO | WO 2014/099750 A2 | 6/2014 |
| WO | WO 2014/172489 A2 | 10/2014 |
| WO | WO 2015/013583 A2 | 1/2015 |
| WO | WO 2015/070083 A1 | 5/2015 |
| WO | WO 2015/077290 A2 | 5/2015 |
| WO | WO 2015/088643 A1 | 6/2015 |
| WO | WO 2015/127439 A1 | 8/2015 |
| WO | WO 2015/163733 A1 | 10/2015 |
| WO | WO 2015/188109 A1 | 12/2015 |
| WO | WO 2015/200805 A2 | 12/2015 |
| WO | WO 2016/011210 A2 | 1/2016 |
| WO | WO 2016/057961 A1 | 4/2016 |
| WO | WO 2016/061374 A1 | 4/2016 |
| WO | WO 2016/065364 A1 | 4/2016 |
| WO | WO 2016/073990 A1 | 5/2016 |
| WO | WO 2016/081923 A2 | 5/2016 |
| WO | WO 2016/094872 A1 | 6/2016 |
| WO | WO 2016/094874 A1 | 6/2016 |
| WO | WO 2016/100819 A1 | 6/2016 |
| WO | WO 2016/112351 A1 | 7/2016 |
| WO | WO 2016/142719 A1 | 9/2016 |

OTHER PUBLICATIONS

"Advance STEM Murine Embryonic Stem Cell Culture Products," Thermoscientific, p. 27, 2010/2011.*
"Generation of Human Induced Pluripotent Stem cells (hiPSCs) from fibroblasts using Episomal Vectors," Invitrogen, pp. 1-14, Jan. 23, 2014.*
"Maintenance of Human iPS cells in a Feeder-Free Culture System," Corning, pp. 1-8, 2012.*
Abudayyeh et al., "C2c2 is a single-component programmable RNA-guided RNA-targeting CRISPR effector," Science, vol. 353(6299), Jun. 2, 2016.
Auerbach et al., "Establishment and chimera analysis of 129/SvEv- and C57BL/6-derived mouse embryonic stem cell lines," Biotechniques, vol. 29(5), pp. 1024-1028, 1030, 1032, Nov. 2000.
Chen, "iPSC derivation from fibroblast in chemically defined medium," STEMBOOK, Jun. 13, 2012.
Choulika et al., "Induction of Homologous Recombination in Mammalian Chromosomes by Using the I-Scel System of Saccharomyces cerevisiae," Mol. Cell. Biol., vol. 15(4), pp. 1968-1973, 1995.
D'Aiuto et al., "Large-scale generation of human iPSC-derived neural stem cells/early neural progenitor cells and their neuronal differentiation," Organogenesis, vol. 10(4), pp. 365-377, Oct. 2, 2014.
Donoho et al., "Analysis of Gene Targeting and Intrachromosomal Homologous Recombination Stimulated by Genomic Double-Strand Breaks in Mouse Embryonic Stem Cells," Mol. Cell. Biol., vol. 18(7), pp. 4070-4078, 1998.
Evers et al., "CRISPR knockout screening outperforms shRNA and CRISPRi in identifying essential genes," Nature Biotechnology, vol. 24(6), pp. 631-633, Apr. 25, 2016.
Frendewey ,"VelociGene: Large-scale Modification of Rodent Genomes," Wellcome Trust Advanced Course: Genetic Engineering of Mammalian Stem Cells, Mar. 13, 2014.
Frendewey, "VelociGene: Large-scale Modification of Rodent Genomes," Wellcome Trust Advanced Course: Genetic Engineering of Mammalian Stem Cells, Feb. 20, 2015.
Gao et al., "DNA-guided genome editing using the Natronobacterium gregoryi Argonaute," Nature Biotechnology, vol. 34(7), pp. 768-773, May 2, 2016.
Hirano et al., "Human and Mouse Induced Pluripotent Stem Cells Are Differentially Reprogrammed in Response to Kinase Inhibitors," Stem Cells and Development, vol. 21(8), pp. 1287-1298, May 20, 2012.
Komor et al, "Programmable editing of a target base in genomic DNA without double-stranded cleavage," Nature, vol. 533(7603), pp. 420-424, Apr. 20, 2016.
Kondo et al., "Protein kinase A-mediated enhancement of miniature IPSC frequency by noradrenaline in rat cerebellar stellate cells," The Journal of Physiology, vol. 498(1), pp. 165-176, Jan. 1, 1997.
Konermann et al., "Genome-scale transcriptional activation by an engineered CRISPR-Cas9 complex," Nature, vol. 517(7536), pp. 583-588, published online Dec. 10, 2014.
Mali, et al., "Cas9 as a versatile tool for engineering biology," Nature Methods, vol. 10(10), pp. 957-963, 2013.
Morgens et al., "Systematic comparison of CRISPR/Cas9 and RNAi screens for essential genes," Nature Biotechnology, vol. 34(6), pp. 634-636, May 9, 2016.
Musser, "Rodent," Brittanica. Retrieved from the Internet May 31, 2016: http://www.brittanica.com/animal/rodent.
PCT International Preliminary Report on Patentability for application PCT/US2014/060788 dated Jun. 23, 2016.
PCT International Search Report and Written Opinion of the International Searching Authority for application PCT/US2015/055776 dated Jan. 29, 2016.
Porteus, et al,, "Gene targeting using zinc finger nucleases," Nature Biotechnology, vol. 23(8), pp. 967-973, 2005.
Ran et al., "In vivo genome editing using Staphylococcus aureus Cas9," Nature, vol. 520(7546), pp. 186-191, Apr. 1, 2015.
Tong et al., "Generating gene knockout rats by homologous recombination in embryonic stem cells," Nature Protocols, vol. 6(6), pp. 827-844, 2011 (epub May 26, 2011).
U.S. Appl. No. 14/515,503, Non-Final Office Action dated May 20, 2016.
U.S. Appl. No. 14/515,503, Notice of Allowance dated Sep. 23, 2016.
U.S. Appl. No. 14/515,503, Requirement for Restriction/Election dated Mar. 4, 2016.
U.S. Appl. No. 14/928,180, Advisory Action dated Aug. 22, 2016.
U.S. Appl. No. 14/928,180, Final Office Action dated Jun. 6, 2016.
U.S. Appl. No. 14/928,180, Non-Final Office Action dated Jan. 5, 2016.
"Stem Cells: Scientific Progress and Future Research Directions," National Institute of Health, Department of Health and Human Services, (2001).
Bernart, et al., "Frozen storage of Ham's F-10 medium for human in-vitro fertilization," Human Reproduction, 5:610-612 (1990).
Byrne et al., "Multi-kilobase homozygous targeted gene replacement in human induced pluripotent stem cells," Nucleic Acids Research, Vo. 43(3), p. e21, 2014 (epub Nov. 20, 2014).
Certificate of Analysis for KNOCKOUT™ DMEM, Life Technologies, Catalog No. 10829, Lot No. 1677060, May 21, 2015.
Chen et al., "Chemically defined conditions for human iPSC derivation and culture," Nature Methods, vol. 8(5), pp. 424-429 plus supplementary materials, 2011 (epub Apr. 20, 2011).
Cheng, et al., "Improved generation of C57BL/6J mouse embryonic stem cells in a defined serum-free media,"Genesis, Jun. 2004, vol. 39(2):100-104.
Cong et al., "Multiplex Genome Engineering Using CRISPR/Cas Systems," Science, vol. 339(6121), pp. 819-823 plus Supplemental Materials, Jan. 3, 2013.
Doudna et al., "The new frontier of genome engineering with CRISPR-Cas9," Science, vol. 346(6213), pp. 1258096-1-1258096-9, Nov. 28, 2014.
Gafni et al.,"Derivation of novel human ground state naïve pluripotent stem cells," Nature, vol. 504(7479), p. 282-286 plus supplementary materials, 2013 (epub Oct. 30, 2013).
Hanna et al., "Human embryonic stem cells with biological and epigenetic characteristics similar to those of mouse ESCs," Proc. Natl. Acad. Sci. U.S.A., vol. 107(20), pp. 9222-9227 plus supplementary materials, 2010 (epub May 4, 2010).

(56) References Cited

OTHER PUBLICATIONS

Kallos, et al., "Inoculation and Growth Conditions for High-Cell-Density Expansion of mannalian Neural Stem Cells in Suspension Bioreactors," Bioengineering, 63:473-483 (1999).

Kuno et al., "Generation of fertile and fecund F0 XY female mice from XY ES cells," Transgenic Research, vol. 24(1), pp. 19-29, 2014 (epub Aug. 3, 2014).

Mali et al., "RNA-Guided Human Genome Engineering via Cas9," Science, vol. 339(6121), pp. 823-826 plus Supplemental Materials, Jan. 3, 2013.

Narsinh, et al., "Gene Correction in Human Embryonic and Induced Pluripotent Stem Cells: Promise and Challenges Ahead", Molecular Therapy, vol. 18, No. 6, pp. 1061-1063, (Jun. 2010).

PCT International Search Report and Written Opinion of the International Searching Authority for application PCT/US2014/060788 dated Jan. 26, 2015.

Perez et al., "Establishment of HIV-1 resistance in CD4+ T cells by genome editing using zinc finger nucleases," Nature Biotech., vol. 26(7), pp. 808-816, 2008.

Schwank, G., et al., "Functional Repair of CFTR by CRISPR/Cas9 in Intestinal Stem Cell Organoids of Cystic Fibrosis Patients," Cell Stem Cell (2013), vol. 13, pp. 653-658.

Singh et al., "A Mouse Geneticist's Practical Guide to CRISPR Applications," Genetics, vol. 199, pp. 1-15, (2015).

Technical Manual, Maintenance of Human Pluripotent Stem Cells in mTeSRtn, Version 4.1.0, Document 29106, Copyright by STEMCELL Technologies, Inc. 2015.

U.S. Appl. No. 14/578,291, Non-Final Office Action dated Mar. 10, 2015.

U.S. Appl. No. 14/578,291, Notice of Allowance dated Aug. 26, 2015.

Ward et al., "The 5T4 oncofoetal antigen is an early differentiation marker of mouse ES cells and its absence is a means to assess pluripotency," The Journal of Cell Science, vol. 116:4533-4542 (Nov. 15, 2003).

Watanabe et al., "A ROCK inhibitor permits survival of dissociated human embryonic stem cells," Nature Biotechnology, vol. 25(6), pp. 681-686, 2007 (epub May 27, 2007).

Yang et al., "Optimization of scarless human stem cell genome editing," Nucleic Acids Res., vol. 41(19), pp. 9049-9061, 2013 (epub Jul. 31, 2013).

Yang et al., "Targeted and genome-wide sequencing reveal single nucleotide variations impacting specificity of Cas9 in human stem cells," Nat. Commun., vol. 5, p. 5507, (2014).

Chin, et al., "Induced Pluripotent Stem Cells and Embryonic Stem Cells Are Distinguished by Gene Expression Signatures," Cell Stem Cell, 5:111-123, (Jul. 2, 2009).

Narsinh, et al., "Comparison of Human Induced Pluripotent and Embryonic Stem Cells: Fraternal or Identical Twins?," Molecular Therapy, vol. 19, No. 4, pp. 635-638, (Apr. 2011).

Buehr, et al., "Capture of Authentic Embryonic Stem Cells from Rat Blastocysts," Cell, 135:1287-1298, (Dec. 26, 2008).

Hu, et al., "Generation of Naivetropic Induced Pluripotent Stem Cells from Parkinson's Disease Patients for High-Efficiency Genetic Manipulation and Disease Modeling," Stem Cells and Development, 24(21):2591-2604, (2015).

Life Technologies, Essential 8tm Medium and Vitronectin FAQs, Life Technologies Corporation (2013).

Nichols, et al., "Naïve and Primed Pluripotent States," Cell Stem Cell 4:487-492, (Jun. 5, 2009).

Ying, et al., "Defined Conditions for Neural Commitment and Differentiation," Methods in Enzymology, 365:327-341, (2003).

Ying, et al., "The ground state of embryonic stem cell self-renewal," Nature, 453:519-523 plus Methods, (May 22, 2008).

Kosicki et al., "Repair of double-strand breaks induced by CRISPR-Cas9 leads to large deletions and complex rearrangements," Nat. Biotechnol., 36(8): 765-771, (Jul. 16, 2018).

Davidson, et al. "The pluripotent state in mouse and human," Development 142(18):3090-3099, (Sep. 15, 2015).

* cited by examiner

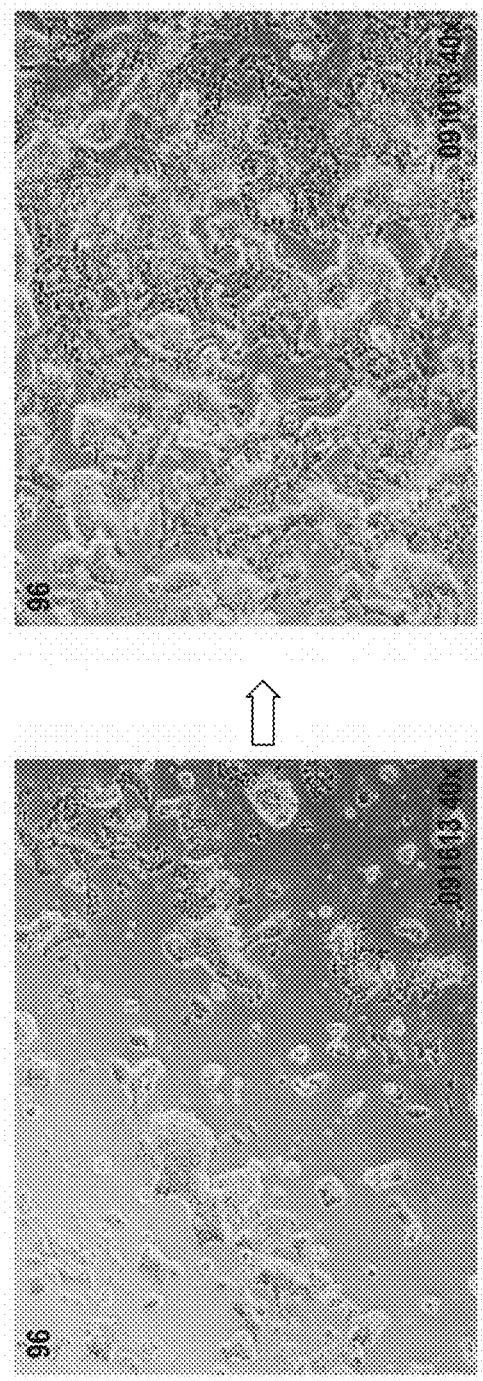
FIG. 2A  8 days in 2i
FIG. 2B  12 days in 2i

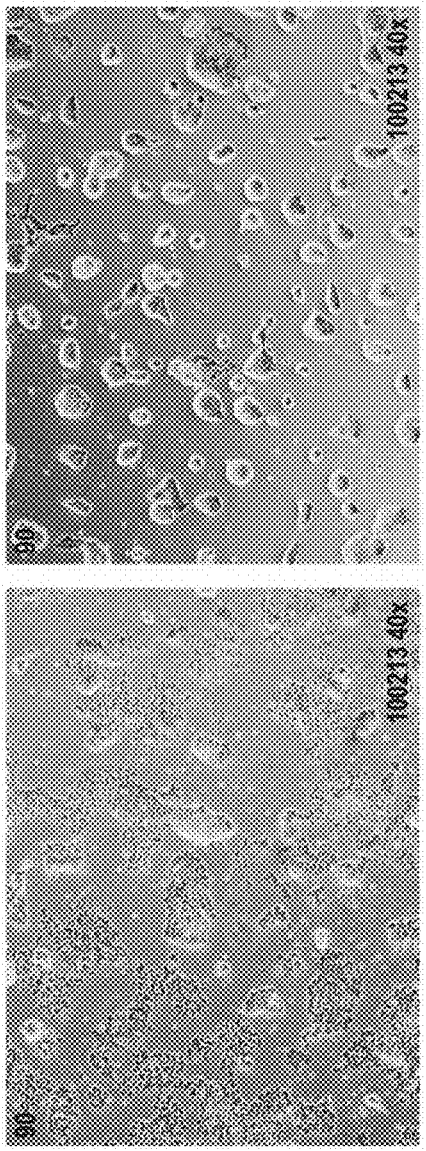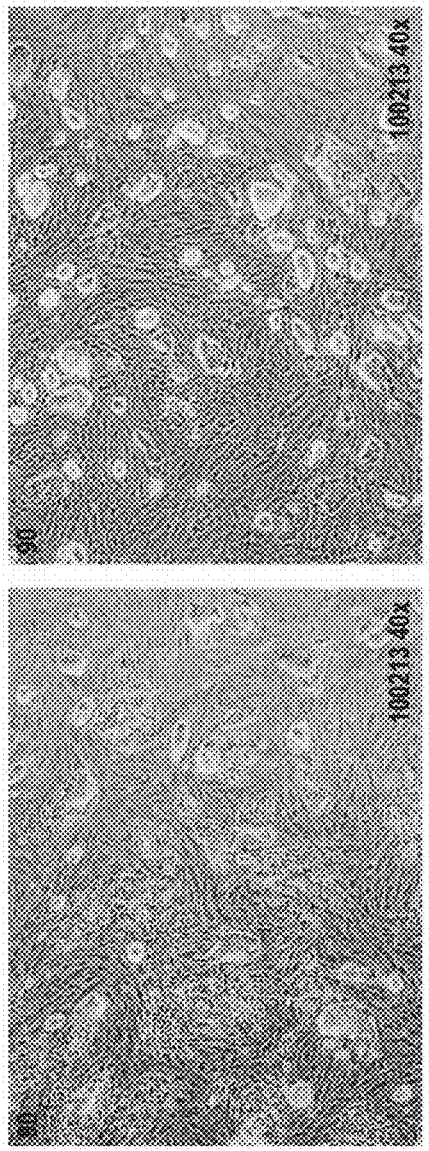
FIG. 3A  mTeSR-hLIF  Matrigel
FIG. 3B  hVG2i  Matrigel
FIG. 3C  mTeSR-hLIF  NuFF feeder
FIG. 3D  hVG2i  NuFF feeder

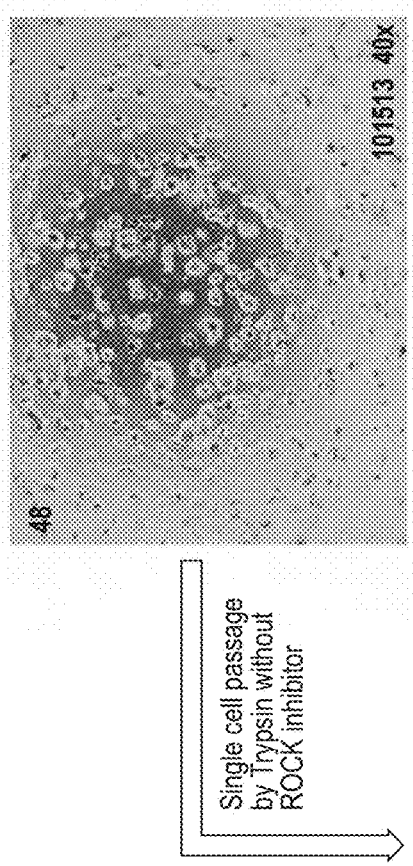
FIG. 5A
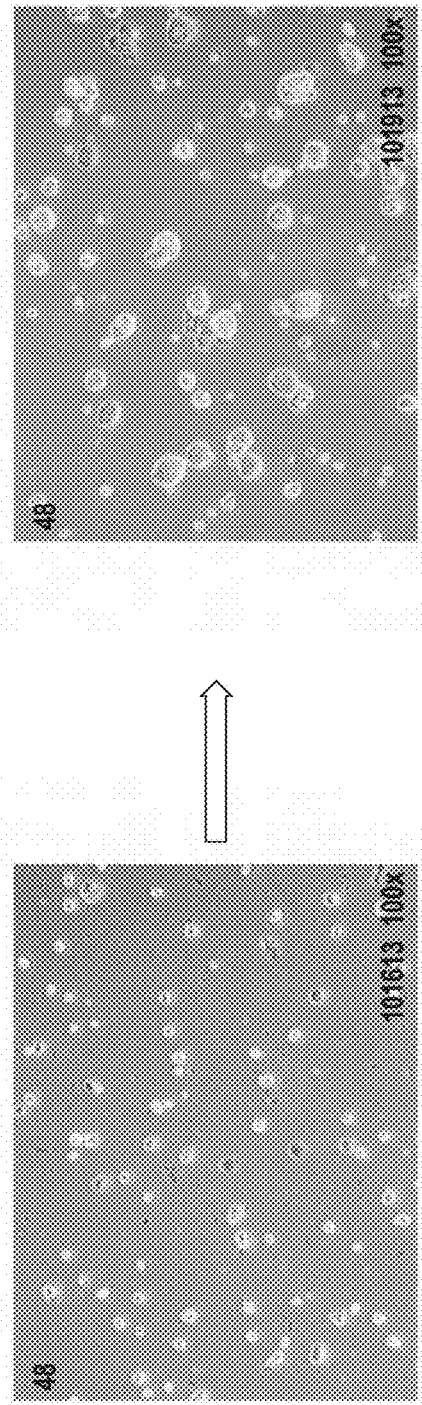
Single cell passage by Trypsin without ROCK inhibitor
FIG. 5B
1 day after passage
FIG. 5C
4 days after passage

METHODS AND COMPOSITIONS FOR GENERATING OR MAINTAINING PLURIPOTENT CELLS

CROSS REFERENCE TO RELATED APPLICATIONS

This application claims the benefit of U.S. Patent Application No. 62/064,384, filed Oct. 15, 2014, which is herein incorporated by reference in its entirety for all purposes.

REFERENCE TO A SEQUENCE LISTING SUBMITTED AS A TEXT FILE VIA EFS WEB

The official copy of the sequence listing is submitted electronically via EFS-Web as an ASCII formatted sequence listing with a file named 469586SEQLIST.TXT, created on Oct. 14, 2015, and having a size of 758 bytes, and is filed concurrently with the specification. The sequence listing contained in this ASCII formatted document is part of the specification and is herein incorporated by reference in its entirety.

BACKGROUND

Human induced pluripotent stem (iPS) cells can display a naïve or primed state of pluripotency (Nichols and Smith, Cell Stem Cell (2009) Vol. 4(6), pp. 487-492). Primed human iPS cells express characteristics similar to those of post-implantation epiblast cells, and are committed for lineage specification and differentiation. By contrast, naïve human iPS cells express characteristics similar to those of embryonic stem (ES) cells of the inner cell mass of a pre-implantation embryo. In some respects, naïve iPS cells are more pluripotent than primed cells, as they are not committed for lineage specification. Various culture conditions can be used to maintain human iPS in a naïve state or in a primed state.

SUMMARY

Methods are provided for making a population of human induced pluripotent stem cells (hiPSCs). Such methods comprise culturing in vitro a population of non-pluripotent cells, transformed to express a pluripotent state, in a low osmolality medium comprising a base medium and supplements, wherein the low osmolality medium comprises: (a) a leukemia inhibitory factor (LIF) polypeptide; (b) a glycogen synthase kinase 3 (GSK3) inhibitor; and (c) a MEK inhibitor; wherein the medium has an osmolality of about 175 mOsm/kg to about 280 mOsm/kg. Such methods can also comprise culturing in vitro a population of non-pluripotent cells, transformed to express a pluripotent state, in a low osmolality medium comprising a base medium and supplements, wherein the low osmolality medium comprises: (a) a leukemia inhibitory factor (LIF) polypeptide; (b) a glycogen synthase kinase 3 (GSK3) inhibitor; and (c) a MEK inhibitor; wherein the base medium has an osmolality of about 180 mOsm/kg to about 250 mOsm/kg.

Further provided are methods for maintaining a population of hiPSCs in an in vitro culture, the methods comprising culturing the population of hiPSCs in a low osmolality medium comprising a base medium and supplements, wherein the low osmolality medium comprises: (a) a leukemia inhibitory factor (LIF) polypeptide; (b) a glycogen synthase kinase 3 (GSK3) inhibitor; and (c) a MEK inhibitor; wherein the medium has an osmolality of about 175 mOsm/kg to about 280 mOsm/kg. Such methods can also comprise culturing the population of hiPSCs in a low osmolality medium comprising a base medium and supplements, wherein the low osmolality medium comprises: (a) a leukemia inhibitory factor (LIF) polypeptide; (b) a glycogen synthase kinase 3 (GSK3) inhibitor; and (c) a MEK inhibitor; wherein the base medium has an osmolality of about 180 mOsm/kg to about 250 mOsm/kg.

In some methods, the hiPSCs comprise naïve or naïve-looking hiPSCs. In some methods, the hiPSCs comprise naïve-like hiPSCs.

In some methods, the method enriches for a population of naïve or naïve-looking hiPSCs. In some methods, the method enriches for a population of naïve-like hiPSCs.

In some methods, the transformed cells express reprogramming genes comprising Oct4, Sox2, Klf4, Myc, or any combination thereof. In some methods, the transformed cells comprise primed hiPSCs.

In some methods, the base medium has an osmolality of about 200 mOsm/kg. In some methods, the base medium comprises NaCl at about 3 mg/ml, sodium bicarbonate at about 2.2 mg/mL, and has an osmolality of about 200 mOsm/kg.

In some methods, the base medium comprises glucose at about 4.5 mg/mL.

In some methods, the low osmolality medium has an osmolality of about 200 mOsm/kg to about 250 mOsm/kg. In some methods, the low osmolality medium has an osmolality of about 233 mOsm/kg.

In some methods, the supplements comprise: (a) F-12 medium; (b) N2 supplement; (c) NEUROBASAL medium; (d) B-27 supplement; (e) L-glutamine; (f) 2-mercaptoethanol; or (g) any combination of (a) to (f).

In some methods, the LIF polypeptide is a human LIF (hLIF) polypeptide. In some methods, the GSK3 inhibitor comprises CHIR99021. In some methods, the MEK inhibitor comprises PD0325901. In some methods, the low osmolality medium comprises inhibitors consisting essentially of a GSK3 inhibitor and a MEK inhibitor.

In some methods, the low osmolality medium comprises base medium at about 24.75% (v/v), F-12 medium at about 24.75% (v/v), N2 supplement at about 0.5% (v/v), NEUROBASAL medium at about 49% (v/v), B-27 supplement at about 1% (v/v), L-glutamine at about 2 mM, 2-mercaptoethanol at about 0.1 mM, hLIF at about 100 units/mL, CHIR99021 at about 3 µM, and PD0325901 at about 0.5 µM.

In some methods, the low osmolality medium does not comprise one or more of the following: bFGF supplement, TGF-β1 supplement, JNK inhibitor, p38 inhibitor, ROCK inhibitor, and PKC inhibitor. In some methods, the low osmolality medium does not comprise basic fibroblast growth factor (bFGF).

In some methods, the hiPSCs or the transformed cells are cultured on MATRIGEL™, newborn human foreskin fibroblast (NuFF) feeder cells, or GELTREX™.

In some methods, the hiPSCs express one or more pluripotency markers. In some methods, the one or more pluripotency markers comprises NANOG, alkaline phosphatase, or a combination thereof. In some methods, the hiPSCs have a normal karyotype.

In some methods, the hiPSCs display a morphology characterized by compact dome-shaped colonies.

In some methods, the hiPSCs can be enzymatically dissociated into a single-cell suspension and subcultured. In some methods, the enzymatic dissociation is performed using trypsin. In some methods, the enzymatic dissociation can be performed in the absence of a Rho-associated protein kinase (ROCK) inhibitor. In some methods, the subcultured hiPSCs continue to express the one or more pluripotency markers. In some methods, the subcultured hiPSCs maintain a naïve or naïve-looking state and display a morphology characterized by compact dome-shaped colonies. In some methods, the subcultured hiPSCs maintain a normal karyotype.

In some methods, the hiPSCs can differentiate into cells of any one of the endoderm, ectoderm, or mesoderm germ layers.

In some methods, the hiPSCs have a doubling time of between about 16 hours and about 24 hours.

In some methods, the transformed cells are first cultured in a high osmolality medium prior to culturing in the low osmolality medium, wherein the high osmolality medium comprises bFGF. Optionally, the high osmolality medium has an osmolality of at least about 290 mOsm/kg.

In some methods, the transformed cells are first cultured in the high osmolality medium until they express characteristics of a naïve or naïve-looking state. In some methods, the transformed cells are first cultured in the high osmolality medium for a period of about two months. In some methods, the transformed cells are first cultured in the high osmolality medium until they display a morphology characterized by three-dimensional cell clumps.

Further provided are hiPSCs made by any of the above methods.

Further provided are methods for modifying a target genomic locus in a hiPSC, comprising: (a) introducing into the hiPSC a targeting vector comprising an insert nucleic acid flanked by 5' and 3' homology arms corresponding to 5' and 3' target sites at the target genomic locus; and (b) identifying a genetically modified hiPSC comprising in its genome the insert nucleic acid integrated at the target genomic locus; wherein the hiPSC is cultured in a low osmolality medium comprising a base medium and supplements, wherein the low osmolality medium comprises: (a) a leukemia inhibitory factor (LIF) polypeptide; (b) a glycogen synthase kinase 3 (GSK3) inhibitor; and (c) a MEK inhibitor; wherein the medium has an osmolality of about 175 mOsm/kg to about 280 mOsm/kg. Such methods can also comprise: (a) introducing into the hiPSC a targeting vector comprising an insert nucleic acid flanked by 5' and 3' homology arms corresponding to 5' and 3' target sites at the target genomic locus; and (b) identifying a genetically modified hiPSC comprising in its genome the insert nucleic acid integrated at the target genomic locus; wherein the hiPSC is cultured in a low osmolality medium comprising a base medium and supplements, wherein the low osmolality medium comprises: (a) a leukemia inhibitory factor (LIF) polypeptide; (b) a glycogen synthase kinase 3 (GSK3) inhibitor; and (c) a MEK inhibitor; wherein the base medium has an osmolality of about 180 mOsm/kg to about 250 mOsm/kg. In some methods, the targeting vector is a large targeting vector (LTVEC), wherein the sum total of the 5' and 3' homology arms is at least 10 kb. In some methods, introducing step (a) further comprises introducing a nuclease agent that promotes homologous recombination between the targeting vector and the target genomic locus in the hiPSC. In some methods, the targeted genetic modification comprises: (a) deletion of an endogenous human nucleic acid sequence; (b) insertion of an exogenous nucleic acid sequence; or (c) replacement of the endogenous human nucleic acid sequence with the exogenous nucleic acid sequence. In some methods, the exogenous nucleic acid sequence comprises one or more of the following: (a) a nucleic acid sequence that is homologous or orthologous to the endogenous human nucleic acid sequence; (b) a chimeric nucleic acid sequence; (c) a conditional allele flanked by site-specific recombinase target sequences; and (d) a reporter gene operably linked to a promoter active in the hiPSC.

Such methods for modifying a target genomic locus in a hiPSC, can also comprise: (a) introducing into the hiPSC one or more nuclease agents that induces one or more nicks or double-strand breaks at a recognition site at the target genomic locus; and (b) identifying at least one cell comprising in its genome a modification at the target genomic locus; wherein the hiPSC is cultured in a low osmolality medium comprising a base medium and supplements, wherein the low osmolality medium comprises: (i) a leukemia inhibitory factor (LIF) polypeptide; (ii) a glycogen synthase kinase 3 (GSK3) inhibitor; and (iii) a MEK inhibitor; wherein the medium has an osmolality of about 175 mOsm/kg to about 280 mOsm/kg. Such methods can also comprise: (a) introducing into the hiPSC one or more nuclease agents that induces one or more nicks or double-strand breaks at a recognition site at the target genomic locus; and (b) identifying at least one cell comprising in its genome a modification at the target genomic locus; wherein the hiPSC is cultured in a low osmolality medium comprising a base medium and supplements, wherein the low osmolality medium comprises: (i) a leukemia inhibitory factor (LIF) polypeptide; (ii) a glycogen synthase kinase 3 (GSK3) inhibitor; and (iii) a MEK inhibitor; wherein the base medium has an osmolality of about 180 mOsm/kg to about 250 mOsm/kg.

In any such methods for modifying a target genomic locus in a hiPSC, the hiPSCs can be enzymatically dissociated into a single-cell suspension and subcultured prior to step (a). Optionally, the enzymatic dissociation is performed using trypsin. Optionally, the enzymatic dissociation is performed in the absence of a ROCK inhibitor. In some methods, the subcultured hiPSCs continue to express one or more pluripotency markers. In some methods, the subcultured hiPSCs maintain a naïve or naïve-looking state and display a morphology characterized by compact dome-shaped colonies. In some methods, the subcultured hiPSCs maintain a normal karyotype.

In some methods, the nuclease agent comprises a zinc finger nuclease (ZFN). In some methods, the nuclease agent comprises a Transcription Activator-Like Effector Nuclease (TALEN). In some methods, the nuclease agent comprises a Clustered Regularly Interspaced Short Palindromic Repeats (CRISPR) associated (Cas) protein and a guide RNA (gRNA) comprising a CRISPR RNA (crRNA) that recognizes a genomic target sequence and a trans-activating CRISPR RNA (tracrRNA). Optionally, the Cas protein is Cas9.

In some methods, the targeted genetic modification is biallelic.

In some methods, the hiPSCs comprise naïve or naïve-looking hiPSCs. In some methods, the hiPSCs comprise naïve-like hiPSCs. In some methods, the hiPSCs express one or more pluripotency markers. Optionally, the pluripotency markers comprise NANOG, alkaline phosphatase, or a combination thereof. In some methods, the hiPSCs display a morphology characterized by compact dome-shaped colonies. In some methods, the hiPSCs can differentiate into cells of any one of the endoderm, ectoderm, or mesoderm germ layers. In some methods, the hiPSCs have a doubling time of between about 16 hours and about 24 hours. In some methods, the hiPSCs have a normal karyotype.

In some methods, the hiPSCs are derived from non-pluripotent cells transformed to express a pluripotent state. Optionally, the transformed cells express reprogramming genes comprising Oct4, Sox2, Klf4, Myc, or any combination thereof. Optionally, the transformed cells comprise primed hiPSCs. In some methods, the transformed cells are first cultured in a high osmolality medium prior to culturing in the low osmolality medium, wherein the high osmolality medium comprises bFGF. Optionally, the high osmolality medium has an osmolality of at least 290 mOsm/kg. In some methods, the transformed cells are first cultured in the high osmolality medium until they express characteristics of a naïve or naïve-looking state. In some methods, the transformed cells are first cultured in the high osmolality medium for a period of about two months. In some methods, the transformed cells are first cultured in the high osmolality medium until they display a morphology characterized by three-dimensional cell clumps.

In some methods, the base medium has an osmolality of about 200 mOsm/kg. In some methods, the base medium comprises NaCl at about 3 mg/ml, sodium bicarbonate at about 2.2 mg/mL, and has an osmolality of about 200 mOsm/kg.

In some methods, the base medium comprises glucose at about 4.5 mg/mL.

In some methods, the low osmolality medium has an osmolality of about 200 mOsm/kg to about 250 mOsm/kg. In some methods, the low osmolality medium has an osmolality of about 233 mOsm/kg.

In some methods, the supplements comprise: (i) F-12 medium; (ii) N2 supplement; (iii) NEUROBASAL medium; (iv) B-27 supplement; (v) L-glutamine; (vi) 2-mercaptoethanol; or (vii) any combination of (i) to (vi). In some methods, the LIF polypeptide is a human LIF (hLIF) polypeptide. In some methods, the GSK3 inhibitor comprises CHIR99021. In some methods, the MEK inhibitor comprises PD0325901.

In some methods, the low osmolality medium comprises inhibitors consisting essentially of a glycogen synthase kinase 3 (GSK3) inhibitor and a MEK inhibitor.

In some methods, the low osmolality medium comprises base medium at about 24.75% (v/v), F-12 medium at about 24.75% (v/v), N2 supplement at about 0.5% (v/v), NEUROBASAL medium at about 49% (v/v), B-27 supplement at about 1% (v/v), L-glutamine at about 2 mM, 2-mercaptoethanol at about 0.1 mM, hLIF at about 100 units/mL, CHIR99021 at about 3 µM, and PD0325901 at about 0.5 µM.

In some methods, the low osmolality medium does not comprise one or more of the following: bFGF supplement; TGF-β1 supplement; JNK inhibitor; p38 inhibitor; ROCK inhibitor; and PKC inhibitor. In some methods, the low osmolality medium does not comprise bFGF supplement.

In some methods, the hiPSCs are cultured on MATRIGEL, NuFF feeder cells, or GELTREX.

Further provided are modified hiPSCs made by any of the above methods.

Further provided are in vitro cultures comprising: (a) a population of hiPSCs; and (b) a low osmolality medium comprising a base medium and supplements, wherein the low osmolality medium comprises: (i) a leukemia inhibitory factor (LIF) polypeptide; (ii) a glycogen synthase kinase 3 (GSK3) inhibitor; and (iii) a MEK inhibitor; wherein the medium has an osmolality of about 175 mOsm/kg to about 280 mOsm/kg. Such in vitro cultures can also comprise (a) a population of hiPSCs; and (b) a low osmolality medium comprising a base medium and supplements, wherein the low osmolality medium comprises: (i) a leukemia inhibitory factor (LIF) polypeptide; (ii) a glycogen synthase kinase 3 (GSK3) inhibitor; and (iii) a MEK inhibitor; wherein the base medium has an osmolality of about 180 mOsm/kg to about 250 mOsm/kg.

Further provided are populations of hiPSCs made or maintained in a low osmolality medium comprising a base medium and supplements, wherein the low osmolality medium comprises: (a) a leukemia inhibitory factor (LIF) polypeptide; (b) a glycogen synthase kinase 3 (GSK3) inhibitor; and (c) a MEK inhibitor; wherein the medium has an osmolality of about 175 mOsm/kg to about 280 mOsm/kg. Such populations of hiPSCs can also be made or maintained in a low osmolality medium comprising a base medium and supplements, wherein the low osmolality medium comprises: (a) a leukemia inhibitory factor (LIF) polypeptide; (b) a glycogen synthase kinase 3 (GSK3) inhibitor; and (c) a MEK inhibitor; wherein the base medium has an osmolality of about 180 mOsm/kg to about 250 mOsm/kg.

In some populations or in vitro cultures, the hiPSCs comprise naïve or naïve-looking hiPSCs. In some populations or in vitro cultures, the hiPSCs comprise naïve-like hiPSCs.

In some populations or in vitro cultures, the hiPSCs are derived from non-pluripotent cells transformed to express a pluripotent state. In some populations or in vitro cultures, the transformed cells express reprogramming genes comprising Oct4, Sox2, Klf4, Myc, or any combination thereof. In some populations or in vitro cultures, the transformed cells comprise primed hiPSCs.

In some populations or in vitro cultures, the base medium has an osmolality of about 200 mOsm/kg. In some populations or in vitro cultures, the base medium comprises NaCl at about 3 mg/ml, sodium bicarbonate at about 2.2 mg/mL, and has an osmolality of about 200 mOsm/kg.

In some populations or in vitro cultures, the base medium comprises glucose at about 4.5 mg/mL.

In some populations or in vitro cultures, the low osmolality medium comprising the base medium and supplements has an osmolality of about 200 mOsm/kg to about 250 mOsm/kg. In some populations or in vitro cultures, the low osmolality medium has an osmolality of about 233 mOsm/kg.

In some populations or in vitro cultures, the supplements comprise: (a) F-12 medium; (b) N2 supplement; (c) NEUROBASAL medium; (d) B-27 supplement; (e) L-glutamine; (f) 2-mercaptoethanol; or (g) any combination of (a) to (f).

In some populations or in vitro cultures, the LIF polypeptide is a human LIF (hLIF) polypeptide. In some populations or in vitro cultures, the GSK3 inhibitor comprises CHIR99021. In some populations or in vitro cultures, the MEK inhibitor comprises PD0325901. In some populations or in vitro cultures, the low osmolality medium comprises inhibitors consisting essentially of a GSK3 inhibitor and a MEK inhibitor.

In some populations or in vitro cultures, the low osmolality medium comprises base medium at about 24.75% (v/v), F-12 medium at about 24.75% (v/v), N2 supplement at about 0.5% (v/v), NEUROBASAL medium at about 49% (v/v), B-27 supplement at about 1% (v/v), L-glutamine at about 2 mM, 2-mercaptoethanol at about 0.1 mM, hLIF at about 100 units/mL, CHIR99021 at about 3 µM, and PD0325901 at about 0.5 µM.

In some populations or in vitro cultures, the low osmolality medium does not comprise one or more of the following: bFGF supplement, TGF-β1 supplement, JNK inhibitor, p38 inhibitor, ROCK inhibitor, and PKC inhibitor.

In some populations or in vitro cultures, the low osmolality medium does not comprise basic fibroblast growth factor (bFGF).

In some populations or in vitro cultures, the hiPSCs or the transformed cells are cultured on MATRIGEL™, newborn human foreskin fibroblast (NuFF) feeder cells, or GELTREX™.

In some populations or in vitro cultures, the hiPSCs express one or more pluripotency markers. In some populations or in vitro cultures, the one or more pluripotency markers comprises NANOG, alkaline phosphatase, or a combination thereof. In some populations or in vitro cultures, the hiPSCs have a normal karyotype.

In some populations or in vitro cultures, the hiPSCs display a morphology characterized by compact dome-shaped colonies.

In some populations or in vitro cultures, the hiPSCs can be enzymatically dissociated into a single-cell suspension and subcultured. In some populations or in vitro cultures, the enzymatic dissociation is performed using trypsin. In some populations or in vitro cultures, the enzymatic dissociation can be performed in the absence of a Rho-associated protein kinase (ROCK) inhibitor. In some populations or in vitro cultures, the subcultured hiPSCs continue to express the one or more pluripotency markers. In some populations or in vitro cultures, the subcultured hiPSCs maintain a naïve or naïve-looking state and display a morphology characterized by compact dome-shaped colonies. In some populations or in vitro cultures, the subcultured hiPSCs maintain a normal karyotype.

In some populations or in vitro cultures, the hiPSCs can differentiate into cells of any one of the endoderm, ectoderm, or mesoderm germ layers.

In some populations or in vitro cultures, the hiPSCs have a doubling time of between about 16 hours and about 24 hours.

In some populations or in vitro cultures, the transformed cells are first cultured in a high osmolality medium prior to culturing in the low osmolality medium, wherein the high osmolality medium comprises bFGF. Optionally, the high osmolality medium has an osmolality of at least about 290 mOsm/kg.

In some populations or in vitro cultures, the transformed cells are first cultured in the high osmolality medium until they express characteristics of a naïve or naïve-looking state. In some populations or in vitro cultures, the transformed cells are first cultured in the high osmolality medium for a period of about two months. In some populations or in vitro cultures, the transformed cells are first cultured in the high osmolality medium until they display a morphology characterized by three-dimensional cell clumps.

BRIEF DESCRIPTION OF THE FIGURES

FIG. 2A depicts the morphology displayed by human iPS cells cultured for 8 days in 2i medium.

FIG. 2B depicts the morphology displayed by human iPS cells cultured for 12 days in 2i medium.

FIGS. 3A-3D depict the morphology of human iPS cells cultured in mTeSR™-hLIF medium or low osmolality VG2i medium for 6 days. FIGS. 3A and 3B depict the morphology of human iPS cells cultured in mTeSR™-hLIF medium (FIG. 3A) or VG2i medium (FIG. 3B) for 6 days. FIGS. 3C and 3D depict the morphology of human iPS cells cultured on newborn human foreskin fibroblast (NuFF) feeder cells in mTeSR™-hLIF medium (FIG. 3C) or VG2i medium (FIG. 3D) for 6 days.

FIGS. 5A-5C illustrate enzymatic dissociation and subculture of reprogrammed human iPS cells cultured in VG2i medium. FIG. 5A depicts reprogrammed human iPS cells cultured in VG2i medium prior to enzymatic dissociation with trypsin in the absence of a ROCK inhibitor. FIG. 5B depicts human iPS cells cultured in VG2i medium for 1 day after subculture. FIG. 5C depicts human iPS cells cultured in VG2i medium for 4 days after subculture.

BRIEF DESCRIPTION OF THE SEQUENCES

Figure 1:
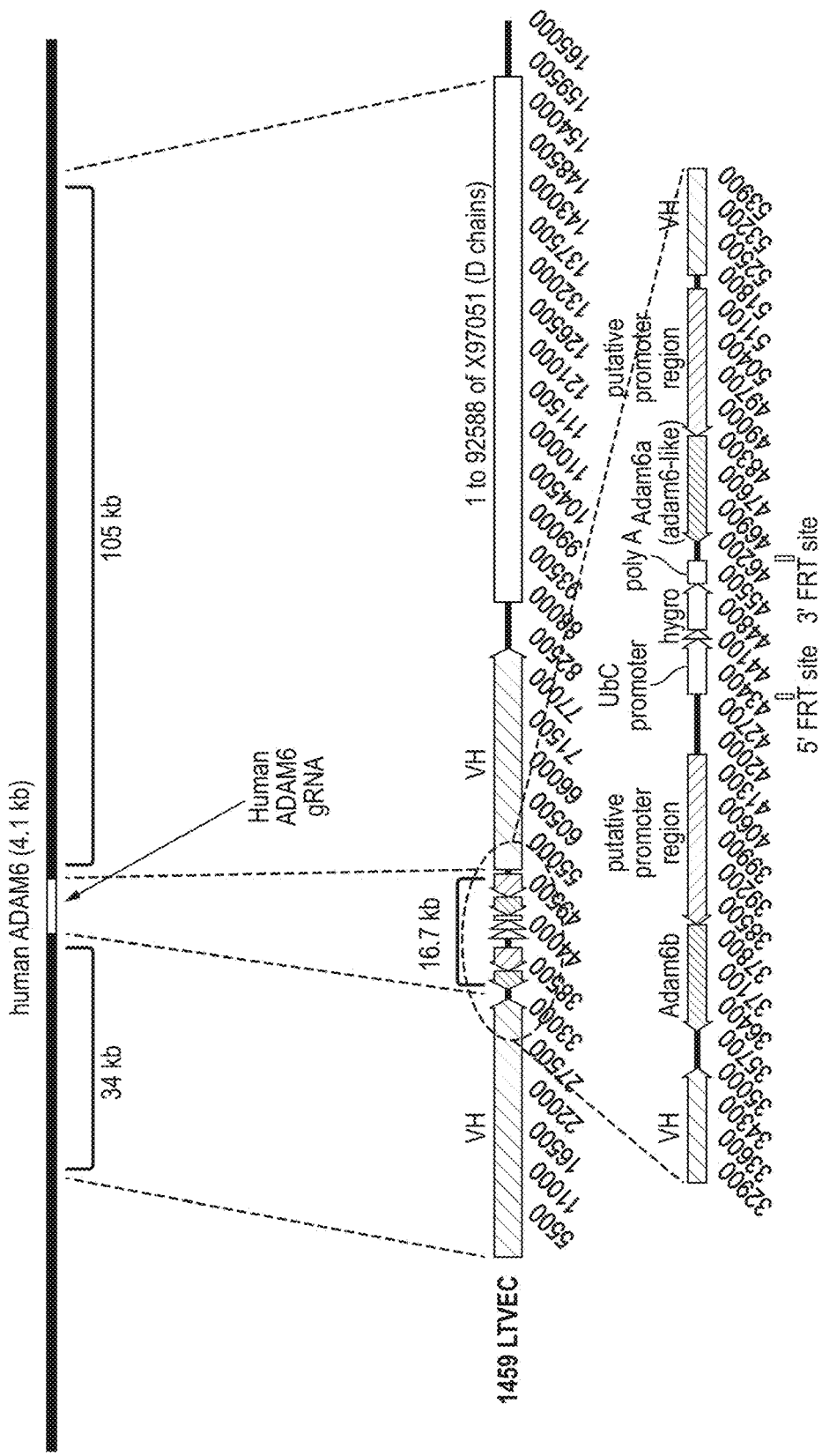
FIG. 1 depicts a schematic for replacement of a portion of the human ADAM6 locus with a nucleic acid comprising the mouse Adam6a and mouse Adam6b loci using an LTVEC and a guide RNA in human iPS cells. The target site for the guide RNA is indicated by the arrow.

SEQ ID NO: 1 sets forth a nucleic acid sequence comprised by ADAM6 gRNA.

SEQ ID NO: 2 sets forth the nucleic acid sequence of a target sequence for a CRISPR/Cas complex.

Definitions

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones.

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

"Codon optimization" generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a nucleic acid encoding a Cas protein can be modified to substitute codons having a higher frequency of usage in a human cell. Codon usage tables are readily available, for example, at the "Codon Usage Database." These tables can be adapted in a number of ways. See Nakamura et al. (2000) Nucleic Acids Research 28:292. Computer algorithms for codon optimization of a particular sequence for expression in a particular host are also available (see, e.g., Gene Forge).

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors.

"Complementarity" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm of hybridized strands, or by empirical determination of Tm by using routine methods. Tm includes the temperature at which a population of hybridization complexes formed between two nucleic acid strands are 50% denatured. At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+0.41(% G+C), although other known Tm computations take into account nucleic acid structural characteristics.

"Hybridization condition" includes the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment. See, e.g., Sambrook et al., Molecular Cloning, A Laboratory Manual, 2.sup.nd ed., pp. 1.90-1.91, 9.47-9.51, 1 1.47-11.57 (Cold Spring Harbor Laboratory Press, Cold Spring Harbor, N.Y., 1989).

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g., complementarity over 35 or fewer, 30 or fewer, 25 or fewer, 22 or fewer, 20 or fewer, or 18 or fewer nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid include at least about 15 nucleotides, at least about 20 nucleotides, at least about 22 nucleotides, at least about 25 nucleotides, and at least about 30 nucleotides. Furthermore, the temperature and wash solution salt concentration may be adjusted as necessary according to factors such as length of the region of complementation and the degree of complementation.

The sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide (e.g., gRNA) can comprise at least 70%, at least 80%, at least 90%, at least 95%, at least 99%, or 100% sequence complementarity to a target region within the target nucleic acid sequence to which they are targeted. For example, a gRNA in which 18 of 20 nucleotides are complementary to a target region, and would therefore specifically hybridize, would represent 90% complementarity. In this example, the remaining noncomplementary nucleotides may be clustered or interspersed with complementary nucleotides and need not be contiguous to each other or to complementary nucleotides.

Percent complementarity between particular stretches of nucleic acid sequences within nucleic acids can be determined routinely using BLAST programs (basic local alignment search tools) and PowerBLAST programs known in the art (Altschul et al. (1990) *J. Mol. Biol.* 215:403-410; Zhang and Madden (1997) *Genome Res.* 7:649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

"Sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

"Percentage of sequence identity" includes the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" includes any sequence comparison program that, for any two sequences in question, generates an alignment having identical nucleotide or amino acid residue matches and an identical percent sequence identity when compared to the corresponding alignment generated by GAP Version 10.

Compositions or methods "comprising" or "including" one or more recited elements may include other elements not specifically recited. For example, a composition that "comprises" or "includes" a protein may contain the protein alone or in combination with other ingredients.

Designation of a range of values includes all integers within or defining the range, and all subranges defined by integers within the range.

The term "about" means that the specified value can vary by some percentage. In some examples, the percentage can be 1, 2, 3, 4, 8, or 10% of the specified value.

The singular forms of the articles "a," "an," and "the" include plural references unless the context clearly dictates otherwise. For example, the term "a cell" or "at least one cell" can include a plurality of cells, including mixtures thereof.

DETAILED DESCRIPTION

A. Low Osmolality Medium for Making and Maintaining Human Induced Pluripotent Stem Cells.

A cell culture medium is provided for use in the methods and compositions of the invention. In one embodiment, the medium is suitable for making a population of human iPS cells. In another embodiment, the medium is suitable for maintaining human iPS cells in culture. In some embodiments, the human iPS cells are naïve or naïve-looking.

The medium provided herein comprises at least a base medium, supplements, a leukemia inhibitory factor (LIF) polypeptide, a glycogen synthase kinase 3 (GSK3) inhibitor, and a mitogen-activated protein kinase kinase (MEK) inhibitor. A "base medium" or "base media" includes, for example, a base medium known in the art (e.g., Dulbecco's Modified Eagle's Medium (DMEM)) that is suitable for use (with added supplements) in growing or maintaining pluripotent cells (e.g., iPS cells) in culture. Base medium is typically supplemented with a number of supplements known in the art when used to maintain cells in culture.

The present medium is a low osmolality medium. In one example, the osmolality is between about 175-280 mOsm/kg. In further examples, the osmolality of the medium is about 180-270 mOsm/kg, about 200-250 mOsm/kg, about 220-240 mOsm/kg, or about 225-235 mOsm. In a particular embodiment, the osmolality of the medium is about 233 mOsm/kg.

The base medium provided for the invention is a low osmolality base medium to which supplements are added. The present base medium differs from base media typically used to maintain human iPS cells in culture, which include Dulbecco's Modified Eagle's Medium (DMEM), in various forms (e.g., Invitrogen DMEM, Cat. No. 1 1971-025), and a low salt DMEM available commercially as KO-DMEM™ (Invitrogen Cat. No. 10829-018).

The base medium provided herein is a low osmolality medium but exhibits characteristics that are not limited to low osmolality. For example, the DMEM formulation shown in Table 1 can be made suitable for the purposes of the invention by altering the sodium chloride and/or sodium bicarbonate concentrations as provided herein, which will result in a different osmolality as compared with the standard DMEM base medium or low-salt DMEM base medium (KO-DMEM) shown in Table 1.

TABLE 1

DMEM base medium formulation.

| Component | Mg/L | mM |
|---|---|---|
| Glycine | 30 | 0.4 |
| L-Arginine•HCl | 84 | 0.398 |
| L-Cystine•2HCl | 63 | 0.201 |
| L-Glutamine | 584 | 4 |
| L-Histidine•HCl•H2O | 42 | 0.2 |
| L-Isoleucine | 105 | 0.802 |
| L-Leucine | 105 | 0.802 |
| L-Lysine•HCl | 146 | 0.798 |
| L-Methionine | 30 | 0.201 |
| L-Phenylalanine | 66 | 0.4 |
| L-Serine | 42 | 0.4 |
| L-Threonine | 95 | 0.798 |
| L-Tryptophan | 16 | 0.0784 |
| L-Tyrosine disodium salt dihydrate | 104 | 0.398 |
| L-Valine | 94 | 0.803 |
| Choline chloride | 4 | 0.0286 |
| D-Calcium pantothenate | 4 | $8.39 \times 10^{-3}$ |
| Folic Acid | 4 | $9.07 \times 10^{-3}$ |
| Niacinamide | 4 | 0.0328 |
| Pyridoxine•HCl | 4 | 0.0196 |
| Riboflavin | 0.4 | $1.06 \times 10^{-3}$ |
| Thiamine•HCl | 4 | 0.0119 |
| i-Inositol | 7.2 | 0.04 |
| Calcium Chloride ($CaCl_2$) (anhydrous) | 200 | 1.8 |
| Ferric Nitrate ($Fe(NO_3)_3$•$9H_2O$) | 0.1 | $2.48 \times 10^{-4}$ |
| Magnesium Sulfate ($MgSO_4$) (anhyd.) | 97.67 | 0.814 |
| Potassium Chloride (KCl) | 400 | 5.33 |
| D-Glucose (Dextrose) | 4500 | 25 |
| Phenol Red | 15 | 0.0399 |
| NaCl/$NaHCO_3$ Content of DMEM | | |
| Sodium Bicarbonate ($NaHCO_3$) | 3700 | 44.05 |
| Sodium Chloride (NaCl) | 6400 | 110.34 |
| Osmolality | | 340 mOsm/kg |
| NaCl/$NaHCO_3$ Content of Low Salt DMEM (KO-DMEM) | | |
| Sodium Bicarbonate ($NaHCO_3$) | 2200 | 26 |
| Sodium Chloride (NaCl) | 5100 | 87.7 |
| Osmolality | | 275 mOsm/kg |
| NaCl/$NaHCO_3$ Content of Low Osmolality DMEM (VG-DMEM) | | |
| Sodium Bicarbonate ($NaHCO_3$) | 2200 | 26 |
| Sodium Chloride (NaCl) | 3000 | 50 |
| Osmolality | | 200 mOsm/kg |

The present base medium can include a salt of an alkaline metal and a halide, such as sodium chloride (NaCl). Exemplary concentrations of NaCl in the base medium include 50±5 mM or about 3 mg/mL. The concentration of a salt of an alkaline metal and a halide in the base medium or a medium comprising the base medium and supplements can be, for example, no more than about 100, 90, 80, 70, 60, or 50 mM. For example, the base medium or a medium comprising the base medium and supplements can comprise a concentration of a salt of an alkaline metal and halide of about 50-110, 60-105, 70-95, 80-90, 90 mM, or 85 mM. Alternatively, the concentration of a salt of an alkaline metal and halide can be, for example, 50±5 mM, 87±5 mM, 110±5 mM, about 3 mg/mL, about 5.1 mg/mL, or about 6.4 mg/mL.

In another embodiment, the base medium exhibits a concentration of a salt of carbonic acid. The salt of carbonic acid can be a sodium salt. In such an example, the sodium salt can be sodium bicarbonate. In a particular embodiment, sodium bicarbonate is present in the base medium at a concentration of about 26±5 mM or about 2.2 mg/mL. The concentration of a salt of carbonic acid in the base medium or a medium comprising the base medium and supplements can be, for example, no more than 45, 40, 35, 30, 25, or 20 mM. For example, the base medium or a medium comprising the base medium and supplements can comprise a concentration of carbonic acid salt in the base medium of about 10-40, 18-44, 17-30, 18-26, 13-25, 20-30, 25-26, 18, or 26 mM. Alternatively, the concentration of carbonic acid salt can be, for example, 18±5 mM, 26±5 mM, about 1.5 mg/mL, or about 2.2 mg/mL.

The sum of the concentration of the salt of the alkaline metal and halide and the salt of carbonic acid in the base medium or a medium comprising the base medium and supplements can be, for example, no more than 140, 130, 120, 110, 100, 90, or 80 mM. For example, the base medium or a medium comprising the base medium and supplements can comprise a sum concentration of a salt of an alkaline metal and halide and a salt of carbonic acid of about 80-140, 85-130, 90-120, 95-120, 100-120, or 115 mM.

The molar ratio of the salt of the alkaline metal and halide and the salt of carbonic acid in the base medium or a medium comprising the base medium and supplements can be, for example, higher than 2.5. For example, the base medium or a medium comprising the base medium and supplements can comprise a molar ratio of a salt of an alkaline metal and halide and a salt of carbonic acid of about 2.6-4.0, 2.8-3.8, 3.0-3.6, 3.2-3.4, 3.3-3.5, or 3.4.

In yet another embodiment, the base medium is a low osmolality base medium. The osmolality of the base medium can be within a range of about 175-280 mOsm/kg, about 180-250 mOsm/kg, about 190-225 mOsm/kg, or about 195-205 mOsm/kg. An exemplary osmolality of the base medium can be 200, 214, 216, or 218 mOsm/kg. In a particular example, the osmolality of the base medium is 200 mOsm/kg. The osmolality can be determined when cells are cultured in different concentrations of CO2. In some examples, cells are cultured at 3% CO2 or 5% CO2. The osmolality of the base medium or a medium comprising the base medium and supplements can be, for example, no more than about 330, 320, 310, 300, 290, 280, 275, 270, 260, 250, 240, 230, 220, 210, or 200 mOsm/kg. For example, the base medium or the medium comprising the base medium and supplements can comprise an osmolality of about 200-329, 218-322, 240-320, 250-310, 275-295, or 260-300 mOsm/kg. For example, the base medium or the medium comprising the base medium and the supplements can comprise an osmolality of about 270 mOsm/kg, about 261 mOsm/kg, or about 218 mOsm/kg. Alternatively, the osmolality can be 218±22 mOsm/kg, 261±26 mOsm/kg, 294±29 mOsm/kg, or 322±32 mOsm/kg.

The osmolality of the base medium can be, for example, about 130-270, 140-260, 150-250, 160-240, 170-230, 180-220, 190-210, 195-205, or 200 mOsm/kg. Alternatively, the osmolality of the base medium can be, for example, about 200±70, 200±60, 200±50, 200±40, 200±35, 200±30, 200±25, 200±20, 200±15, 200±10, 200±5, or 200 mOsm/kg. Alternatively, the osmolality of the base medium can be, for example, about 130-140, about 140-150, about 150-160, about 160-170, about 170-180, about 180-190, about 190-200, about 200-210, about 210-220, about 220-230, about 230-240, about 240-250, about 250-260, about 260-270, about 270-280, about 280-290, about 290-300, about 300-310, about 310-320, or about 320-330 mOsm/kg. Alternatively, the osmolality of the base medium can be, for example, less than about 330, 320, 310, 300, 290, 280, 270, 260, 250, 240, 230, 220, 210, 200, 190, 180, 170, 160, 150, 140, or 130 mOsm/kg.

The osmolality of the medium comprising the base medium and supplements can be, for example, about 205-260, 215-250, 225-240, 230-235, or 233 mOsm/kg. Alternatively, the osmolality of the medium comprising the base medium and supplements can be, for example, about 233±27, 233±25, 233±20, 233±15, 233±10, 233±5, or 233 mOsm/kg. Alternatively, the osmolality of the medium comprising the base medium and supplements can be, for example, about 200-205, 205-210, 210-215, 215-220, 220-225, 225-230, 230-235, 235-240, 240-245, 245-250, 250-255, or 255-260 mOsm/kg. Alternatively, the osmolality of the medium comprising the base medium and supplements can be, for example, less than 260, 255, 250, 245, 240, 235, 230, 225, 220, 215, 210, 205, or 200 mOsm/kg.

In some low osmolality media, the base medium comprises about 87±5 mM NaCl and about 26±5 mM carbonate. For example the base media can comprise about 5.1 mg/mL NaCl, about 2.2 mg/mL sodium bicarbonate, and an osmolality of about 275 mOsm/kg.

In some low osmolality media, the base medium comprises about 50±5 mM NaCl and about 26±5 mM carbonate. For example, the base medium can comprise about 3.0 mg/mL NaCl, about 2.2 mg/mL sodium bicarbonate, and an osmolality of about 200 mOsm/kg. In a preferred embodiment, the base medium comprises NaCl at a concentration of 3.0 mg/mL, sodium bicarbonate at a concentration of about 2.2 mg/mL, and has an osmolality of 200 mOsm/kg.

Other examples of low osmolality media are described in WO 2011/156723, US 2011/0307968, and US 2015/0067901, each of which is herein incorporated by reference in its entirety.

Supplements formulated with the base medium of the invention are suitable for making, maintaining, or enriching populations of human iPS cells disclosed herein. Such supplements are indicated as "supplements" or "+ supplements" in this disclosure. The term "supplements" or the phrase "+ supplements," includes one or more additional elements added to the components of the base medium described in Table 1. For example, supplements can include, without limitation, F-12® medium (Gibco), N2® supplement (Gibco; 100× solution), NEUROBASAL® medium (Gibco), B-27® supplement (Gibco; 50× solution), L-glutamine, glucose, 2-mercaptoethanol, a Leukemia Inhibitory Factor (LIF) polypeptide, a glycogen synthase kinase 3 inhibitor, a MEK inhibitor, or any combination thereof. Supplements can also include, for example, fetal bovine serum (FBS), antibiotic(s), penicillin and streptomycin (i.e., penstrep), pyruvate salts (e.g., sodium pyruvate), and nonessential amino acids (e.g., MEM NEAA).

In a particular embodiment, the LIF polypeptide is a human LIF (hLIF) polypeptide. In some examples, a hLIF polypeptide is used at a concentration of about 1-1000 units/mL, about 20-800 units/mL, about 50-500 units/mL, about 75-250 units/mL, or about 100 units/mL.

The media can comprise inhibitors, for example, consisting essentially of a GSK3 inhibitor and a MEK inhibitor. For example, the medium can comprise inhibitors consisting of a GSK3 inhibitor and a MEK inhibitor.

In another particular embodiment, the GSK3 inhibitor comprises CHIR99021. In some examples, CHIR99021 is used at a concentration of about 0.1 to 10 μM, about 1-5 μM, about 2-4 μM, or about 3 μM.

In another particular embodiment, the MEK inhibitor comprises PD0325901. In some examples, PD0325901 is used at a concentration of about 0.1-5 μM, about 0.2-1 μM, about 0.3-0.7 μM, or about 0.5 μM.

An exemplary medium comprises a low osmolality base medium described herein at about 24.75% (v/v), F-12 medium at about 24.75% (v/v), N2 supplement at about 0.5% (v/v), NEUROBASAL medium at about 49% (v/v), B-27 supplement at about 1% (v/v), L-glutamine at about 2 mM, 2-mercaptoethanol at about 0.1 mM, hLIF at about 100 units/mL, CHIR99021 at about 3 μM, and PD0325901 at about 0.5 μM.

In another particular embodiment, the medium may or may not comprise basic fibroblast growth factor (bFGF, also known as FGF2 or FGF-β1). Preferably the present medium does not comprise bFGF.

The medium may or may not comprise one or more of transforming growth factor beta 1 (TGF-β1) supplement, bFGF supplement, c-Jun N-terminal kinase (JNK) inhibitor (e.g., SP600125), p38 mitogen-activated protein kinase (p38) inhibitor (e.g., SB203580), rho-associated protein kinase (ROCK) inhibitor (e.g., Y-27632), and protein kinase C (PKC) inhibitor (e.g., Go6983). The medium may or may not comprise forskolin. For example, some media do not comprise one or more of TGF-β1 supplement, bFGF supplement, JNK inhibitor (e.g., SP600125), p38 inhibitor (e.g., SB203580), ROCK inhibitor (e.g., Y-27632), and PKC inhibitor (e.g., Go6983). Some media do not comprise one or more of p38 inhibitor and JNK inhibitor. Some media do not comprise bFGF supplement or TGF-β1 supplement. Some media do not comprise TGF-β1 supplement. Some media do not comprise any one of TGF-β1 supplement, bFGF supplement, JNK inhibitor (e.g., SP600125), p38 inhibitor (e.g., SB203580), ROCK inhibitor (e.g., Y-27632), and PKC inhibitor (e.g., Go6983). Some media do not comprise forskolin.

B. Human Induced Pluripotent Stem Cells

Methods and compositions are provided herein for making a population of human iPS cells. Methods and compositions are further provided for maintaining human iPS cells in culture. Human iPS cells that are produced or maintained in culture are also provided.

The term "pluripotent cell" or "pluripotent stem cell" includes an undifferentiated cell that possesses the ability to develop into more than one differentiated cell type. Such pluripotent cells can be, for example, a mammalian embryonic stem (ES cell) cell or a mammalian induced pluripotent stem cell (iPS cell). Examples of pluripotent cells include human iPS cells.

The term "embryonic stem cell" or "ES cell" means an embryo-derived totipotent or pluripotent stem cell, derived from the inner cell mass of a blastocyst, that can be maintained in an in vitro culture under suitable conditions. ES cells are capable of differentiating into cells of any of the three vertebrate germ layers, e.g., the endoderm, the ectoderm, or the mesoderm. ES cells are also characterized by their ability propagate indefinitely under suitable in vitro culture conditions. See, for example, Thomson et al. (Science (1998) Vol. 282(5391), pp. 1145-1147).

The term "induced pluripotent stem cell" or "iPS cell" includes a pluripotent stem cell that can be derived directly from a differentiated adult cell. Human iPS cells can be generated by introducing specific sets of reprogramming factors into a non-pluripotent cell which can include, for example, Oct3/4, Sox family transcription factors (e.g., Sox1, Sox2, Sox3, Sox15), Myc family transcription factors (e.g., c-Myc, l-Myc, n-Myc), Krüppel-like family (KLF) transcription factors (e.g., KLF1, KLF2, KLF4, KLF5), and/or related transcription factors, such as NANOG, LIN28, and/or Glisl. Human iPS cells can also be generated, for example, by the use of miRNAs, small molecules that mimic the actions of transcription factors, or lineage specifiers. Human iPS cells are characterized by their ability to differentiate into any cell of the three vertebrate germ layers, e.g., the endoderm, the ectoderm, or the mesoderm. Human iPS cells are also characterized by their ability propagate indefinitely under suitable in vitro culture conditions. See, for example, Takahashi and Yamanaka (Cell (2006) Vol. 126(4), pp. 663-676).

The terms "naïve" and "primed" identify different pluripotency states of human iPS cells. The term "naïve-looking" identifies a cell expressing a pluripotent state that exhibits one or more characteristics of a naïve pluripotent cell. Naïve-looking human iPS cells can also be referred to as "naïve-like" human iPS cells. The terms "naïve-looking" and "naïve-like" are intended to be equivalent. In some embodiments, naïve-looking human iPS cells exhibit one or more morphological characteristics of naïve human iPS cells, such as a morphology characterized by compact dome-shaped colonies. In some embodiments, naïve-looking human iPS cells express one or more of the pluripotency markers described herein. In some embodiments, naïve or naïve-looking human iPS cells are naïve human iPS cells. In other embodiments, naïve or naïve-looking human iPS cells are naïve-looking iPS cells.

Characteristics of naïve and primed iPS cells are described in the art. See, for example, Nichols and Smith (Cell Stem Cell (2009) Vol. 4(6), pp. 487-492). Naïve human iPS cells exhibit a pluripotency state similar to that of ES cells of the inner cell mass of a pre-implantation embryo. Such naïve cells are not primed for lineage specification and commitment. Female naïve iPS cells are characterized by two active X chromosomes. In culture, self-renewal of naïve human iPS cells is dependent on leukemia inhibitory factor (LIF) and other inhibitors. Cultured naïve human iPS cells display a clonal morphology characterized by rounded dome-shaped colonies and a lack of apico-basal polarity. Cultured naïve cells can further display one or more pluripotency makers as described elsewhere herein. Under appropriate conditions, the doubling time of naïve human iPS cells in culture can be between 16 and 24 hours.

Primed human iPS cells express a pluripotency state similar to that of post-implantation epiblast cells. Such cells are primed for lineage specification and commitment. Female primed iPS cells are characterized by one active X chromosome and one inactive X chromosome. In culture, self-renewal of primed human iPS cells is dependent on fibroblast growth factor (FGF) and activin. Cultured primed human iPS cells display a clonal morphology characterized by an epithelial monolayer and display apico-basal polarity. Under appropriate conditions, the doubling time of primed human iPS cells in culture can be 24 hours or more.

In one embodiment, human iPS cells can be derived from non-pluripotent cells transformed to express a pluripotent state. Such transformed cells include, for example, cells that have been transformed to express reprogramming genes that induce pluripotency. A pluripotent state can include, for example, expression of one or more of the pluripotency markers described herein. Such cells (such as human foreskin fibroblasts) can be transformed to express reprogramming genes, or any additional genes of interest, by any means known in the art. See, for example, Takahashi and Yamanaka (Cell (2006) Vol. 126(4), pp. 663-676). For example, they can be introduced into the cells using one or more plasmids, lentiviral vectors, or retroviral vectors. In some cases, the vectors integrate into the genome and can be removed after reprogramming is complete. In particular embodiments, the non-pluripotent cells are transformed with reprogramming genes comprising Oct4, Sox2, Klf4, Myc, or any combination thereof. In some examples, the transformed cells comprise primed human iPS cells.

In some embodiments, the human iPS cells cultured in the low osmolality medium described herein express one or more phenotypes, gene expression profiles, or markers characteristic of a naïve state. In one example, the human iPS cells express one or more pluripotency markers whose expression is indicative of a naïve state. Such pluripotency markers can include alkaline phosphatase, NANOG, 5T4, ABCG2, Activin RIB/ALK-4, Activin RIIB, E-Cadherin, Cbx2, CD9, CD30/TNFRSF8, CD117/c-kit, CDX2, CHD1, Cripto, DNMT3B, DPPA2, DPPA4, DPPA5/ESG1, EpCAM/TROP1, ERR beta/NR3B2, ESGP, F-box protein 15/FBXO15, FGF-4, FGF-5, FoxD3, GBX2, GCNF/NR6A1, GDF-3, Gi24/VISTA/B7-H5, integrin alpha 6/CD49f, integrin alpha 6 beta 1, integrin alpha 6 beta 4, integrin beta 1/CD29, KLF4, KLF5, L1TD1, Lefty, Lefty-1, Lefty-A, LIN-28A, LIN-28B, LIN-41, cMaf, cMyc, Oct-3/4, Oct-4A, Podocalyxin, Rex-1/ZFP42, Smad2, Smad2/3, SOX2, SSEA-1, SSEA-3, SSEA-4, STAT3, Stella/Dppa3, SUZ12, TBX2, TBX3, TBX5, TERT, TEX19, TEX19.1, THAP11, TRA-1-60(R), TROP-2, UTF1, and/or ZIC3. In a specific example, the expressed pluripotency marker is alkaline phosphatase, NANOG, or both.

In another embodiment, human iPS cells cultured in the low osmolality medium described herein display morphological characteristics indicative of a naïve state. An exemplary morphology is characterized by cells having compact dome-shaped colonies in culture.

The human iPS cells cultured in the low osmolality medium described herein can have a normal karyotype. A normal karyotype includes a karyotype in which all chromosomes normally characteristic of the species are present and have not been noticeably altered or a state of cells lacking any visible numerical or structural chromosomal abnormality detectable with chromosome banding analysis. The human iPS cells cultured in the low osmolality medium described herein can have a normal karyotype, for example, after about 5, 10, 15, 20, 25, 30, 35, 40, 45, 50, 55, 60, 65, 70, 75, 80, 85, 90, 95, or 100 passages in the low osmolality medium described herein.

In another embodiment, human iPS cells cultured in the low osmolality medium described herein can be mechanically or enzymatically dissociated into a single-cell suspension, passaged, and/or subcultured. Such human iPS cells cultured in the low osmolality medium described herein can have a normal karyotype and can maintain the normal karyotype after being mechanically or enzymatically dissociated into a single-cell suspension, passaged, and/or subcultured. For example, such human iPS cells cultured in the low osmolality medium described herein can have a normal karyotype and can maintain the normal karyotype after being mechanically or enzymatically dissociated into a single-cell suspension, modified at a target genomic locus using the methods described elsewhere herein, and subcultured. In one example, enzymatic dissociation can be performed using trypsin.

When cultured in the present low osmolality medium, human iPS cells can provide greater transformation efficiency due to enhanced dissociation into a single-cell suspension. With other types of medium (e.g., mTeSR™ medium or 2i medium) typically used to maintain human iPS cells in culture, dissociation of human iPS cells must be performed mechanically or with enzymes such as collagenase that are less harsh than trypsin. It is generally not recommended to passage human iPS cells as single cells, as this practice has been demonstrated to place unwanted selective pressures on cell populations that can lead to, for example, genetic aberrations in culture. Human iPS cells are vulnerable to apoptosis upon cellular detachment and dissociation, and typically undergo massive cell death after complete dissociation. See Watanabe et al. (2007) Nature 25(6):681-686, herein incorporated by reference in its entirety for all purposes. Thus, dissociation of human iPS cells is typically performed with reagents or methods that minimize the breakup of colonies when passaging and do not create single-cell suspensions. Consequently, the cells are not dissociated as effectively or as completely. However, complete dissociation can be important for procedures such as clonal isolation following gene transfer or generation of a targeted genetic modification, particularly when attempting to isolate relatively rare clones such as those undergoing homologous recombination to produce a desired targeted modification. In contrast, with the present low osmolality medium, trypsin can be used to dissociate the cells, and the enhanced dissociation results in increased transformation efficiency. For example, such dissociation can create single-cell suspensions that result in greater targeting efficiencies when targeting, for example, via electroporation or using the methods for making targeted genetic modifications described elsewhere herein. Furthermore, unlike with other types of medium typically used to maintain human iPS cells in culture (e.g., mTeSR™ medium or 2i medium), enzymatic dissociation of human iPS cells cultured with the present low osmolality medium (preferably a low osmolality medium not comprising bFGF) can be performed in the absence of one or more inhibitors that are generally necessary for the passage of such cells. An exemplary inhibitor that can be omitted is a Rho-associated protein kinase (ROCK) inhibitor. A ROCK inhibitor is generally necessary when passaging human iPS cells to inhibit the activation of pro-apoptotic pathways. In particular, addition of a ROCK inhibitor is generally recommended when plating single-cell suspensions of human iPS cells, as this has been reported to increase cell survival. See Watanabe et al. (2007) *Nature* 25(6):681-686. When using the low osmolality medium disclosed herein, however, such ROCK inhibitors are not needed, even when passaging as single-cell suspensions. Such single-cell suspensions can maintain pluripotency and a normal karyotype following trypsinization and replating when the low osmolality medium disclosed herein is used.

In a further embodiment, subcultured human iPS cells cultured in the low osmolality medium described herein can maintain a naïve or naïve-looking state following enzymatic dissociation and subculture. Subcultured human iPS cells cultured in the low osmolality medium described herein can maintain a naïve or naïve-looking state following enzymatic dissociation and subculture even when passaged as single-cell suspensions and/or when modified at a target genomic locus using the methods described elsewhere herein. In some examples, subcultured human iPS cells can continue to display a morphology characterized by compact dome-shaped colonies. Subcultured human iPS cells can also continue to express one or pluripotency markers as described herein.

C. Methods of Making and Maintaining a Population of Human Induced Pluripotent Stem Cells Methods and compositions are provided for making human iPS cells in an in vitro culture. Methods and compositions are further provided for maintaining human iPS cells in an in vitro culture.

The term "making" includes culturing non-pluripotent cells transformed to express one or more reprogramming factors as described herein, under suitable conditions to induce a change in cell phenotype, gene expression, or both, such that the cells display a naïve or naïve-looking state, i.e., express one or more characteristics of naïve human iPS cells. A naïve or naïve-looking state can be expressed in response to particular culture conditions, e.g., culture in a low osmolality medium as described herein. In some examples, the proportion of cells expressing a naïve or naïve-looking state is at least about 30%, 40%, 50%, 60%, 70%, 80%, 90%, 95%, and up to 100% of the cells in culture.

In one embodiment, the method enriches an in vitro culture for a population of naïve or naïve-looking human iPS cells. In such an embodiment, naïve or naïve-looking human iPS cells can be propagated in culture preferentially over cells that do not express a naïve or naïve-looking state. In another embodiment, naïve or naïve-looking human iPS cells can be selected from a culture, be enzymatically dissociated, and subcultured to produce an enriched population of naïve or naïve-looking human iPS cells.

In one embodiment, non-pluripotent cells transformed to express a pluripotent state, are cultured in vitro in a medium provided herein that is suitable for inducing expression of a naïve or naïve-looking state for a period of at least 1, 2, 5, 7, 10, 14, 21, or 28 days, or any period of time sufficient to induce expression of a naïve or naïve-looking state in culture. Transformed cells can be cultured in the present medium for at least 1, 2, 3, or 4 weeks. Sometimes transformed cells are cultured for 1-4 weeks. Expression of a naïve or naïve-looking state can be determined by observing morphological characteristics or the expression of pluripotency markers, characteristic of a naïve or naïve-looking state, that are described elsewhere herein.

In one embodiment, non-pluripotent cells transformed to express a pluripotent state, are cultured in the present low osmolality medium until they express characteristics of a naïve or naïve-looking state. Cells can then be cultured in the present medium to maintain a naïve or naïve-looking state. In another embodiment, non-pluripotent cells transformed to express a pluripotent state, are first cultured in a high osmolality medium prior to culturing in the present low osmolality medium. Such high osmolality medium exhibits an osmolality higher than the present low osmolality medium and can comprise bFGF. The osmolality of the high osmolality medium can be, for example, about 300-380, 310-370, 320-360, 330-350, or 340 mOsm/kg. Alternatively, the osmolality of the high osmolality medium can be, for example, 340±70, 340±60, 340±50, 340±40, 340±30, 340±20, or 340±10 mOsm/kg. For example, the osmolality of the high osmolality medium can be about 270-280, 280-290, 290-300, 300-310, 310-320, 320-330, 330-340, 340-350, 350-360, 360-370, 370-380, 380-390, 390-400, or 400-410 mOsm/kg. Alternatively, the osmolality of the high osmolality medium can be at least about 270, 280, 290, 300, 310, 320, 330, 340, 350, 360, 370, 380, 390, 400, or 410 mOsm/kg. Some high osmolality medium comprises one or more of bovine serum albumin, bFGF, transforming growth factor β (TGFβ), lithium chloride, pipecolic acid, and gamma-aminobutyric acid (GABA). Examples of a high osmolality medium include mTeSR™ medium (Stemcell Technologies).

In some embodiments, non-pluripotent cells transformed to express a pluripotent state, can first be cultured in high osmolality medium comprising bFGF until they begin to express characteristics of a naïve or naïve-looking state, at which time the cells are cultured in the present low osmolality medium. In one example, cells can be cultured in high osmolality medium comprising bFGF for a period of at least 1, 2, 5, 10, 30, 60, or 90 days, a period of 1, 2, 4, 8, or 12 weeks, or a period between 1 day to 3 months. An exemplary time period for culture in a high osmolality medium comprising bFGF is 2 months.

In other embodiments, non-pluripotent cells transformed to express a pluripotent state, can first be cultured in high osmolality medium comprising bFGF until they begin to display a morphology characterized by three-dimensional cell clumps, at which time cells are cultured in the present low osmolality medium. In such embodiments, cells displaying three-dimensional clumps can be selected, dissociated (e.g., with trypsin), and transferred to a new culture in the low osmolality medium described herein.

The terms "maintain," "maintaining," and "maintenance" include the preservation of at least one or more of the characteristics or phenotypes of the human iPS cells described herein. Such characteristics can include maintaining pluripotency, cell morphology, gene expression profiles, and/or other functional characteristics of naïve cells. The terms "maintain," "maintaining," and "maintenance" can also encompass the propagation of cells and/or an increase in the number of naïve cells being cultured. The terms include culture conditions that prevent cells from converting to a primed or non-pluripotent state. The terms further include culture conditions that permit the cells to remain pluripotent and/or naïve, while the cells may or may not continue to divide and increase in number.

In one embodiment, human iPS cells are cultured in vitro in a medium provided herein that is suitable for maintaining such cells in a naïve or naïve-looking state. In a particular example, human iPS cells can be cultured in a suitable medium for a period of 1, 2, 5, 7, 10, 14, 21, or 28 days, or for a period of about 2 weeks, about 3 weeks, about 4 weeks, or more, so long as the cultured cells are maintained in a naïve or naïve-looking state. Cells can be cultured for at least 1, 2, 3 or 4 weeks. Sometimes cells are cultured for 1-4 weeks. Human iPS cells can be maintained, for example, for any period of time sufficient for propagation of the cells in culture, genetic modification of the cells, and/or subculture of the cells.

In another embodiment, human iPS cells or non-pluripotent cells transformed to express a pluripotent state, can be cultured on a substrate or feeder cell layer suitable for in vitro culture. In a particular example, cells are cultured on MATRIGEL™ (BD Biosciences). In another example, cells are cultured on newborn human foreskin fibroblast (NuFF) feeder cells. In another example, cells are cultured on GELTREX™ (Life Technologies). In another example, the cells are cultured on vitronectin (e.g., VITRONECTIN XF™ (STEMCELL Technologies).

In a further embodiment, the doubling time of human iPS cells cultured in the present low osmolality medium is reduced as compared to primed human iPS cells or non-pluripotent cells transformed to express a pluripotent state.

In a particular example, the doubling time of the present human iPS cells is between about 16-24 hours.

D. Genetic Modifications and Methods for Making Targeted Genetic Modifications

In some embodiments, the methods for making and maintaining human iPS cells comprise introducing a genetic modification into the human iPS cells. Likewise, the invention provides human iPS cells that comprise a genetic modification.

In particular embodiments, the genetic modification comprises a modification of one or more endogenous nucleic acids, a substitution of one or more endogenous nucleic acids, a replacement of an endogenous nucleic acid with a heterologous nucleic acid, a knockout, or a knock-in. In specific examples, the genetic modification is introduced by introducing a large targeting vector (LTVEC) into the human iPS cells or the non-pluripotent cells transformed to express a pluripotent state. In such an example, the LTVEC can comprise DNA to be inserted into the genome of the cells.

Various methods for making targeted genetic modifications in human iPS cells can be used. For example, various methods for making targeted genetic modifications that modify the level and/or the activity of proteins in human iPS cells can be used. For example, in one instance, the targeted genetic modification employs a system that will generate a targeted genetic modification via a homologous recombination (HR) event. Homology-directed repair (HDR) or HR includes a form of nucleic acid repair that can require nucleotide sequence homology, uses a "donor" molecule to template repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. In other instances, a cell can be modified using nuclease agents that generate a single or double strand break at a targeted genomic location. The single or double-strand break is then repaired by the non-homologous end joining pathway (NHEJ). NHEJ includes the repair of double-strand breaks in a nucleic acid by direct ligation of the break ends to one another without the need for a homologous template. Ligation of non-contiguous sequences by NHEJ can often result in deletions, insertions, or translocations near the site of the double-strand break. Such systems find use, for example, in generating targeted loss of function genetic modifications. Non-limiting methods for generating such targeted genetic modification are discussed in detail elsewhere herein, including, for example, the use of targeting plasmids or large targeting vectors. See, also, Wang et al. (2013) Cell 153: 910-918, Mandalos et al. (2012) PLOS ONE 7:e45768:1-9, and Wang et al. (2013) Nat Biotechnol. 31:530-532, each of which is herein incorporated by reference.

It is recognized that in specific embodiments, the targeted genetic modification of any polynucleotide of interest can occur while the pluripotent cell (i.e., human iPS cell) is being maintained in the culture medium described herein. Alternatively, the targeted genetic modification of any polynucleotide of interest can occur while the pluripotent cell (i.e., human iPS cell) is being maintained in different culture medium, and subsequently transferred to the low osmolality culture medium disclosed herein.

In general, the level and/or activity of a protein is modified if the protein level and/or the activity level of the protein is statistically higher or lower than the protein level in an appropriate control cell that has not been genetically modified or mutagenized to alter the expression and/or activity of the protein. In specific embodiments, the concentration and/or activity of the protein is altered by at least 1%, 5%, 10%, 20%, 30%, 40%, 50%, 60%, 70%, 80%, or 90% relative to a control cell which has not been modified to have a modified level and/or activity of the protein.

A "subject cell" is one in which a genetic alteration, such as a genetic modification disclosed herein has been effected, or is a cell which is descended from a cell so altered and which comprises the alteration. A "control" or "control cell" provides a reference point for measuring changes in phenotype of the subject cell. In one embodiment, a control cell is as closely matched as possible with the cell with reduced protein activity except it lacks the genetic modification or mutation resulting in the modified activity (for example, the respective cells can originate from the same cell line). In other instances, the control cell may comprise, for example: (a) a wild-type cell, i.e., of the same genotype as the starting material for the genetic alteration which resulted in the subject cell; (b) a cell of the same genotype as the starting material but which has been genetically modified with a null construct (i.e. with a construct which has no known effect on the trait of interest, such as a construct comprising a marker gene); (c) a cell which is a non-genetically modified progeny of a subject cell (i.e., the control cell and the subject cell originate from the same cell line); (d) a cell genetically identical to the subject cell but which is not exposed to conditions or stimuli that would induce expression of the gene of interest; or (e) the subject cell itself, under conditions in which the genetic modification does not result in an alteration in expression of the polynucleotide of interest.

The expression level of the polypeptide may be measured directly, for example, by assaying for the level of the polypeptide in the cell or organism, or indirectly, for example, by measuring the activity of the polypeptide.

In other instances, cells having the targeted genetic modification are selected using methods that include, but are not limited to, Southern blot analysis, DNA sequencing, PCR analysis, or phenotypic analysis. Such cells are then employed in the various methods and compositions described herein.

A targeted genetic modification can comprise a targeted alteration to a polynucleotide of interest. Such targeted modifications include, but are not limited to, additions of one or more nucleotides, deletions of one or more nucleotides, substitutions of one or more nucleotides, a knockout of the polynucleotide of interest or a portion thereof, a knock-in of the polynucleotide of interest or a portion thereof, a replacement of an endogenous nucleic acid sequence with a heterologous nucleic acid sequence, or a combination thereof. In specific embodiments, at least 1, 2, 3, 4, 5, 7, 8, 9, 10, 100, 500 or more nucleotides or at least 10 kb to 500 kb or more are changed to form the targeted genomic modification.

In other embodiments, the activity and/or level of a polypeptide is modified by introducing into the cell a polynucleotide that alters the level or activity of the polypeptide. The polynucleotide may modify the expression of the polypeptide directly, by altering translation of the messenger RNA, or indirectly, by encoding a polypeptide that alters the transcription or translation of the gene encoding a protein. In other embodiments, the activity of a polypeptide is modified by introducing into the cell a sequence encoding a polypeptide that alters the activity of the target polypeptide.

In one embodiment, human iPS cells can comprise a conditional allele that modifies the activity and/or level of a protein. A "conditional allele" includes a modified gene designed to have the modified level and/or activity of the protein at a desired developmental time and/or within a desired tissue of interest. The modified level and/or activity can be compared with a control cell lacking the modification giving rise to the conditional allele, or in the case of modified activity at a desired developmental time with preceding and/or following times, or in the case of a desired tissue, with a mean activity of all tissues. In one embodiment, the conditional allele comprises a conditional null allele of the gene that can be switched off or on at a desired developmental time point and/or in specific tissues.

In a non-limiting embodiment, the conditional allele is a multifunctional allele, as described in US 2011/0104799, which is incorporated by reference in its entirety. In specific embodiments, the conditional allele comprises: (a) an actuating sequence in sense orientation with respect to transcription of a target gene, and a drug selection cassette (DSC) in sense or antisense orientation; (b) in antisense orientation a nucleotide sequence of interest (NSI) and a conditional by inversion module (COIN, which utilizes an exon-splitting intron and an invertible genetrap-like module; see, for example, US 2011/0104799, which is incorporated by reference in its entirety); and (c) recombinable units that recombine upon exposure to a first recombinase to form a conditional allele that (i) lacks the actuating sequence and the DSC, and (ii) contains the NSI in sense orientation and the COIN in antisense orientation.

The present invention allows for modifying a target genomic locus on a chromosome in a cell. In particular embodiments, the methods provided herein allow for the targeting of a genomic locus on a chromosome by employing a targeting vector in the absence of, or in combination with, a nuclease agent.

Methods for making targeted genetic modifications can comprise, for example, the use of a targeting vector (e.g., an LTVEC), either alone or in combination with one or more nucleases as described elsewhere herein. See, e.g., US 2015/0159175, US 2015/0159174, US 2014/0310828, US 2014/0309487, and US 2013/0309670, each of which is herein incorporated by reference in its entirety for all purposes. Likewise, methods for making targeted genetic modifications can comprise the use of one or more nucleases either alone or in combination with a targeting vector.

For example, methods are provided for modifying a target genomic locus in a human iPS cell, comprising: (a) introducing into the cell one or more nuclease agents that induces one or more nicks or double-strand breaks at a recognition site at or near the target genomic locus; and (b) identifying at least one cell comprising in its genome a modification at the target genomic locus. Such methods can result in disruption of the target genomic locus. Disruption of the endogenous nucleic acid sequence can result, for example, when a double-strand break created by a nuclease is repaired by non-homologous end joining (NHEJ)-mediated DNA repair, which generates a mutant allele comprising an insertion or a deletion of a nucleic acid sequence and thereby causes disruption of that genomic locus. Examples of disruption include alteration of a regulatory element (e.g., promoter or enhancer), a missense mutation, a nonsense mutation, a frame-shift mutation, a truncation mutation, a null mutation, or an insertion or deletion of small number of nucleotides (e.g., causing a frameshift mutation). Disruption can result in inactivation (i.e., loss of function) or loss of the allele.

Other methods for modifying a target genomic locus in a human iPS cell comprise: (a) introducing into the cell a targeting vector comprising an insert nucleic acid flanked by 5' and 3' homology arms corresponding to 5' and 3' target sites; and (b) identifying at least one cell comprising in its genome the insert nucleic acid integrated at the target genomic locus.

Other methods for modifying a target genomic locus in a human iPS cell comprise: (a) introducing into the cell: (i) a nuclease agent, wherein the nuclease agent induces a nick or double-strand break at a recognition site within the target genomic locus; and (ii) a targeting vector comprising an insert nucleic acid flanked by 5' and 3' homology arms corresponding to 5' and 3' target sites located in sufficient proximity to the recognition site; and (c) identifying at least one cell comprising a modification (e.g., integration of the insert nucleic acid) at the target genomic locus. Such methods can result in various types of targeted genetic modifications. Such targeted modifications can include, for example, additions of one or more nucleotides, deletions of one or more nucleotides, substitutions of one or more nucleotides, a point mutation, a knockout of a polynucleotide of interest or a portion thereof, a knock-in of a polynucleotide of interest or a portion thereof, a replacement of an endogenous nucleic acid sequence with a heterologous, exogenous, or orthologous nucleic acid sequence, a domain swap, an exon swap, an intron swap, a regulatory sequence swap, a gene swap, or a combination thereof. For example, at least 1, 2, 3, 4, 5, 7, 8, 9, 10 or more nucleotides can be changed to form the targeted genomic modification. The deletions, insertions, or replacements can be of any size, as disclosed elsewhere herein.

a. Nuclease Agents and Recognition Sites for Nuclease Agents

The term "recognition site for a nuclease agent" includes a DNA sequence at which a nick or double-strand break is induced by a nuclease agent. The recognition site for a nuclease agent can be endogenous (or native) to the cell or the recognition site can be exogenous to the cell. In specific embodiments, the recognition site is exogenous to the cell and thereby is not naturally occurring in the genome of the cell. In still further embodiments, the recognition site is exogenous to the cell and to the polynucleotides of interest that one desired to be positioned at the target locus. In further embodiments, the exogenous or endogenous recognition site is present only once in the genome of the host cell. In specific embodiments, an endogenous or native site that occurs only once within the genome is identified. Such a site can then be used to design nuclease agents that will produce a nick or double-strand break at the endogenous recognition site.

The length of the recognition site can vary and includes, for example, recognition sites that are about 30-36 by for a zinc finger nuclease (ZFN) pair (i.e., about 15-18 by for each ZFN), about 36 by for a Transcription Activator-Like Effector Nuclease (TALEN), or about 20 by for a CRISPR/Cas9 guide RNA.

In one embodiment, each monomer of the nuclease agent recognizes a recognition site of at least 9 nucleotides. In other embodiments, the recognition site is from about 9 to about 12 nucleotides in length, from about 12 to about 15 nucleotides in length, from about 15 to about 18 nucleotides in length, or from about 18 to about 21 nucleotides in length, and any combination of such subranges (e.g., 9-18 nucleotides). It is recognized that a given nuclease agent can bind the recognition site and cleave that binding site or alternatively, the nuclease agent can bind to a sequence that is different from the recognition site. Moreover, the term recognition site comprises both the nuclease agent binding site and the nick/cleavage site irrespective whether the nick/cleavage site is within or outside the nuclease agent binding site. In another variation, the cleavage by the nuclease agent can occur at nucleotide positions immediately opposite each other to produce a blunt end cut or, in other cases, the incisions can be staggered to produce single-stranded overhangs, also called "sticky ends", which can be either 5' overhangs, or 3' overhangs.

Any nuclease agent that induces a nick or double-strand break into a desired recognition site can be used in the methods and compositions disclosed herein. A naturally-occurring or native nuclease agent can be employed so long as the nuclease agent induces a nick or double-strand break in a desired recognition site. Alternatively, a modified or engineered nuclease agent can be employed. An "engineered nuclease agent" includes a nuclease that is engineered (modified or derived) from its native form to specifically recognize and induce a nick or double-strand break in the desired recognition site. Thus, an engineered nuclease agent can be derived from a native, naturally-occurring nuclease agent or it can be artificially created or synthesized. The modification of the nuclease agent can be as little as one amino acid in a protein cleavage agent or one nucleotide in a nucleic acid cleavage agent. In some embodiments, the engineered nuclease induces a nick or double-strand break in a recognition site, wherein the recognition site was not a sequence that would have been recognized by a native (non-engineered or non-modified) nuclease agent. Producing a nick or double-strand break in a recognition site or other DNA can be referred to herein as "cutting" or "cleaving" the recognition site or other DNA.

Active variants and fragments of the exemplified recognition sites are also provided. Such active variants can comprise at least 65%, 70%, 75%, 80%, 85%, 90%, 91%, 92%, 93%, 94%, 95%, 96%, 97%, 98%, 99% or more sequence identity to the given recognition site, wherein the active variants retain biological activity and hence are capable of being recognized and cleaved by a nuclease agent in a sequence-specific manner Assays to measure the double-strand break of a recognition site by a nuclease agent are known in the art (e.g., TaqMan® qPCR assay, Frendewey D. et al., Methods in Enzymology, 2010, 476: 295-307, which is incorporated by reference herein in its entirety).

The recognition site of the nuclease agent can be positioned anywhere in or near the target locus. The recognition site can be located within a coding region of a gene, or within regulatory regions that influence expression of the gene. A recognition site of the nuclease agent can be located in an intron, an exon, a promoter, an enhancer, a regulatory region, or any non-protein coding region. In specific embodiments, the recognition site is positioned within the polynucleotide encoding the selection marker. Such a position can be located within the coding region of the selection marker or within the regulatory regions, which influence the expression of the selection marker. Thus, a recognition site of the nuclease agent can be located in an intron of the selection marker, a promoter, an enhancer, a regulatory region, or any non-protein-coding region of the polynucleotide encoding the selection marker. In specific embodiments, a nick or double-strand break at the recognition site disrupts the activity of the selection marker. Methods to assay for the presence or absence of a functional selection marker are known.

In one embodiment, the nuclease agent is a Transcription Activator-Like Effector Nuclease (TALEN). TAL effector nucleases are a class of sequence-specific nucleases that can be used to make double-strand breaks at specific target sequences in the genome of a prokaryotic or eukaryotic organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) PNAS 10.1073/pnas.1013133107; Scholze & Boch (2010) Virulence 1:428-432; Christian et al. Genetics (2010) 186:757-761; Li et al. (2010) Nuc. Acids Res. (2010) doi:10.1093/nar/gkq704; and Miller et al. (2011) Nature Biotechnology 29:143-148; all of which are herein incorporated by reference.

Examples of suitable TAL nucleases, and methods for preparing suitable TAL nucleases, are disclosed, e.g., in US Patent Application No. 2011/0239315 A1, 2011/0269234 A1, 2011/0145940 A1, 2003/0232410 A1, 2005/0208489 A1, 2005/0026157 A1, 2005/0064474 A1, 2006/0188987 A1, and 2006/0063231 A1 (each hereby incorporated by reference). In various embodiments, TAL effector nucleases are engineered that cut in or near a target nucleic acid sequence in, e.g., a locus of interest or a genomic locus of interest, wherein the target nucleic acid sequence is at or near a sequence to be modified by a targeting vector. The TAL nucleases suitable for use with the various methods and compositions provided herein include those that are specifically designed to bind at or near target nucleic acid sequences to be modified by targeting vectors as described herein.

In one embodiment, each monomer of the TALEN comprises 12-25 TAL repeats, wherein each TAL repeat binds a 1 by subsite. In some TALENs, each monomer of the TALEN comprises 33-35 TAL repeats that recognize a single base pair via two hypervariable residues. In one embodiment, the nuclease agent is a chimeric protein comprising a TAL repeat-based DNA binding domain operably linked to an independent nuclease. In one embodiment, the independent nuclease is a FokI endonuclease. In one embodiment, the nuclease agent comprises a first TAL-repeat-based DNA binding domain and a second TAL-repeat-based DNA binding domain, wherein each of the first and the second TAL-repeat-based DNA binding domains is operably linked to a FokI nuclease, wherein the first and the second TAL-repeat-based DNA binding domain recognize two contiguous target DNA sequences in each strand of the target DNA sequence separated by about 6 by to about 40 by cleavage site, and wherein the FokI nucleases dimerize and make a double strand break at a target sequence. For example, the nuclease agent can comprise a first TAL-repeat-based DNA binding domain and a second TAL-repeat-based DNA binding domain, wherein each of the first and the second TAL-repeat-based DNA binding domains is operably linked to a FokI nuclease, wherein the first and the second TAL-repeat-based DNA binding domain recognize two contiguous target DNA sequences in each strand of the target DNA sequence separated by a spacer sequence of varying length (12-20 bp), and wherein the FokI nuclease subunits dimerize to create an active nuclease that makes a double strand break at a target sequence.

The nuclease agent employed in the various methods and compositions disclosed herein can further comprise a zinc-finger nuclease (ZFN). In one embodiment, each monomer of the ZFN comprises 3 or more zinc finger-based DNA binding domains, wherein each zinc finger-based DNA binding domain binds to a 3 by subsite. In other embodiments, the ZFN is a chimeric protein comprising a zinc finger-based DNA binding domain operably linked to an independent nuclease. In one embodiment, the independent endonuclease is a FokI endonuclease. In one embodiment, the nuclease agent comprises a first ZFN and a second ZFN, wherein each of the first ZFN and the second ZFN is operably linked to a FokI nuclease, wherein the first and the second ZFN recognize two contiguous target DNA sequences in each strand of the target DNA sequence separated by about 6 by to about 40 by cleavage site, and wherein the FokI nucleases dimerize and make a double strand break. For example, the nuclease agent can comprise a first ZFN and a second ZFN, wherein each of the first ZFN and the second ZFN is operably linked to a FokI nuclease subunit, wherein the first and the second ZFN recognize two contiguous target DNA sequences in each strand of the target DNA sequence separated by about 5-7 by spacer, and wherein the FokI nuclease subunits dimerize to create an active nuclease that makes a double strand break. See, for example, US20060246567; US20080182332; US20020081614; US20030021776; WO/2002/057308A2; US20130123484; US20100291048; and, WO/2011/017293A2, each of which is herein incorporated by reference.

In still another embodiment, the nuclease agent is a meganuclease. Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. Meganucleases are notable for their long recognition sites, and for tolerating some sequence polymorphisms in their DNA substrates. Meganuclease domains, structure and function are known, see for example, Guhan and Muniyappa (2003) Crit Rev Biochem Mol Biol 38:199-248; Lucas et al., (2001) Nucleic Acids Res 29:960-9; Jurica and Stoddard, (1999) Cell Mol Life Sci 55:1304-26; Stoddard, (2006) Q Rev Biophys 38:49-95; and Moure et al., (2002) Nat Struct Biol 9:764. In some examples a naturally occurring variant, and/or engineered derivative meganuclease is used. Methods for modifying the kinetics, cofactor interactions, expression, optimal conditions, and/or recognition site specificity, and screening for activity are known, see for example, Epinat et al., (2003) Nucleic Acids Res 31:2952-62; Chevalier et al., (2002) Mol Cell 10:895-905; Gimble et al., (2003) Mol Biol 334:993-1008; Seligman et al., (2002) Nucleic Acids Res 30:3870-9; Sussman et al., (2004) J Mol Biol 342:31-41; Rosen et al., (2006) Nucleic Acids Res 34:4791-800; Chames et al., (2005) Nucleic Acids Res 33:e178; Smith et al., (2006) Nucleic Acids Res 34:e149; Gruen et al., (2002) Nucleic Acids Res 30:e29; Chen and Zhao, (2005) Nucleic Acids Res 33:e154; WO2005105989; WO2003078619; WO2006097854; WO2006097853; WO2006097784; and WO2004031346.

Any meganuclease can be used herein, including, but not limited to, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-SeaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any active variants or fragments thereof.

In one embodiment, the meganuclease recognizes double-stranded DNA sequences of 12 to 40 base pairs. In one embodiment, the meganuclease recognizes one perfectly matched target sequence in the genome. In one embodiment, the meganuclease is a homing nuclease. In one embodiment, the homing nuclease is a LAGLIDADG family of homing nuclease. In one embodiment, the LAGLIDADG family of homing nuclease is selected from I-SceI, I-CreI, and I-DmoI.

Nuclease agents can further comprise restriction endonucleases, which include Type I, Type II, Type III, and Type IV endonucleases. Type I and Type III restriction endonucleases recognize specific recognition sites, but typically cleave at a variable position from the nuclease binding site, which can be hundreds of base pairs away from the cleavage site (recognition site). In Type II systems the restriction activity is independent of any methylase activity, and cleavage typically occurs at specific sites within or near to the binding site. Most Type II enzymes cut palindromic sequences, however Type IIa enzymes recognize non-palindromic recognition sites and cleave outside of the recognition site, Type IIb enzymes cut sequences twice with both sites outside of the recognition site, and Type IIs enzymes recognize an asymmetric recognition site and cleave on one side and at a defined distance of about 1-20 nucleotides from the recognition site. Type IV restriction enzymes target methylated DNA. Restriction enzymes are further described and classified, for example in the REBASE database (webpage at rebase.neb.com; Roberts et al., (2003) Nucleic Acids Res 31:418-20), Roberts et al., (2003) Nucleic Acids Res 31:1805-12, and Belfort et al., (2002) in Mobile DNA II, pp. 761-783, Eds. Craigie et al., (ASM Press, Washington, D.C.).

The nuclease agent employed in the various methods and compositions can also comprise a Clustered Regularly Interspersed Short Palindromic Repeats (CRISPR)/CRISPR-associated (Cas) system or components of such a system. CRISPR/Cas systems include transcripts and other elements involved in the expression of, or directing the activity of, Cas genes. A CRISPR/Cas system can be a type I, a type II, or a type III system. The methods and compositions disclosed herein employ CRISPR/Cas systems by utilizing CRISPR complexes (comprising a guide RNA (gRNA) complexed with a Cas protein) for site-directed cleavage of nucleic acids.

Some CRISPR/Cas systems used in the methods disclosed herein are non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR/Cas systems employ non-naturally occurring CRISPR complexes comprising a gRNA and a Cas protein that do not naturally occur together.

Cas proteins generally comprise at least one RNA recognition or binding domain. Such domains can interact with guide RNAs (gRNAs, described in more detail below). Cas proteins can also comprise nuclease domains (e.g., DNase or RNase domains), DNA binding domains, helicase domains, protein-protein interaction domains, dimerization domains, and other domains. A nuclease domain possesses catalytic activity for nucleic acid cleavage. Cleavage includes the breakage of the covalent bonds of a nucleic acid molecule. Cleavage can produce blunt ends or staggered ends, and it can be single-stranded or double-stranded.

Examples of Cas proteins include Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, CsaS, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csxl, Csx15, Csf1, Csf2, Csf3, Csf4, and Cu1966, and homologs or modified versions thereof.

In some instances, a Cas protein is from a type II CRISPR/Cas system. For example, the Cas protein can be a Cas9 protein or be derived from a Cas9 protein. Cas9 proteins typically share four key motifs with a conserved architecture. Motifs 1, 2, and 4 are RuvC-like motifs, and motif 3 is an HNH motif. The Cas9 protein can be from, for example, *Streptococcus pyogenes, Streptococcus thermophilus, Streptococcus sp., Nocardiopsis dassonvillei, Streptomyces pristinaespiralis, Streptomyces viridochromogenes, Streptomyces viridochromogenes, Streptosporangium roseum, Streptosporangium roseum, AlicyclobacHlus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas sp., Crocosphaera watsonii, Cyanothece sp., Microcystis aeruginosa, Synechococcus sp., Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter sp., Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc sp., Arthrospira maxima, Arthrospira platensis, Arthrospira sp., Lyngbya sp., Microcoleus chthonoplastes, Oscillatoria sp., Petrotoga mobilis, Thermosipho africanus,* or *Acaryochloris marina.* The Cas9 protein can be from *Staphylococcus aureus.* Additional examples of the Cas9 family members include those described in WO 2014/131833, herein incorporated by reference in its entirety. In a specific example, the Cas9 protein is a Cas9 protein from *S. pyogenes* or is derived therefrom. The amino acid sequence of a Cas9 protein from *S. pyogenes* can be found, for example, in the SwissProt database under accession number Q99ZW2.

Cas proteins can be wild type proteins (i.e., those that occur in nature), modified Cas proteins (i.e., Cas protein variants), or fragments of wild type or modified Cas proteins. Cas proteins can also be active variants or fragments of wild type or modified Cas proteins. Active variants or fragments can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

Cas proteins can be modified to increase or decrease nucleic acid binding affinity, nucleic acid binding specificity, and/or enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity of the Cas protein.

Some Cas proteins comprise at least two nuclease domains, such as DNase domains. For example, a Cas9 protein can comprise a RuvC-like nuclease domain and an HNH-like nuclease domain. The RuvC and HNH domains can each cut a different strand of double-stranded DNA to make a double-stranded break in the DNA. See, e.g., Jinek et al. (2012) Science 337:816-821, hereby incorporated by reference in its entirety.

One or both of the nuclease domains can be deleted or mutated so that they are no longer functional or have reduced nuclease activity. If one of the nuclease domains is deleted or mutated, the resulting Cas protein (e.g., Cas9) can be referred to as a nickase and can generate a single strand break at a target sequence within a double-stranded DNA but not a double strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA. An example of a mutation that converts Cas9 into a nickase is a D10A (aspartate to alanine at position 10 of Cas9) mutation in the RuvC domain of Cas9 from *S. pyogenes.* Likewise, H939A (histidine to alanine at amino acid position 839) or H840A (histidine to alanine at amino acid position 840) in the HNH domain of Cas9 from *S. pyogenes* can convert the Cas9 into a nickase. Other examples of mutations that convert Cas9 into a nickase include the corresponding mutations to Cas9 from *S. thermophilus.* See, e.g., Sapranauskas et al. (2011) Nucleic Acids Research 39:9275-9282 and WO 2013/141680, each of which is herein incorporated by reference in its entirety. Such mutations can be generated using well-known methods such as site-directed mutagenesis, PCR-mediated mutagenesis, or total gene synthesis. Examples of other mutations creating nickases can be found, for example, in WO/2013/176772A1 and WO/2013/142578A1, each of which is herein incorporated by reference.

Cas proteins can also be fusion proteins. For example, a Cas protein can be fused to a cleavage domain, an epigenetic modification domain, a transcriptional activation domain, or a transcriptional repressor domain. See WO 2014/089290, incorporated herein by reference in its entirety. Cas proteins can also be fused to a heterologous polypeptide providing increased or decreased stability. The fused domain or heterologous polypeptide can be located at the N-terminus, the C-terminus, or internally within the Cas protein.

One example of a Cas fusion protein is a Cas protein fused to a heterologous polypeptide that provides for subcellular localization. Such sequences can include, for example, a nuclear localization signal (NLS) such as the SV40 NLS for targeting to the nucleus, a mitochondrial localization signal for targeting to the mitochondria, an ER retention signal, and the like. See, e.g., Lange et al. (2007) *J. Biol. Chem.* 282:5101-5105. Such subcellular localization signals can be located at the N-terminus, the C-terminus, or anywhere within the Cas protein. An NLS can comprise a stretch of basic amino acids, and can be a monopartite sequence or a bipartite sequence.

Cas proteins can also comprise a cell-penetrating domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, for example, WO 2014/089290, herein incorporated by reference in its entirety. The cell-penetrating domain can be located at the N-terminus, the C-terminus, or anywhere within the Cas protein.

Cas proteins can also comprise a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreenl), yellow fluorescent proteins (e.g., YFP, eYFP, Citrine, Venus, YPet, PhiYFP, ZsYellowl), blue fluorescent proteins (e.g. eBFP, eBFP2, Azurite, mKalamal, GFPuv, Sapphire, T-sapphire), cyan fluorescent proteins (e.g. eCFP, Cerulean, CyPet, AmCyanl, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRedl, AsRed2, eqFP611, mRaspberry, mStrawberry, Jred), orange fluorescent proteins (mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AUS, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin.

Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism (i.e., a human cell). When a nucleic acid encoding the Cas protein is introduced into the cell, the Cas protein can be transiently, conditionally, or constitutively expressed in the cell.

Nucleic acids encoding Cas proteins can be stably integrated in the genome of the cell and operably linked to a promoter active in the cell. Alternatively, nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a targeting vector comprising a nucleic acid insert and/or a vector comprising a DNA encoding the gRNA. Alternatively, it can be in a vector or a plasmid that is separate from the targeting vector comprising the nucleic acid insert and/or separate from the vector comprising the DNA encoding the gRNA. Promoters that can be used in an expression construct include, for example, promoters active in a human iPS cell or a non-pluripotent cell transformed to express a naïve state. Such promoters can be, for example, conditional promoters, inducible promoters, constitutive promoters, or tissue-specific promoters.

A "guide RNA" or "gRNA" includes an RNA molecule that binds to a Cas protein and targets the Cas protein to a specific location within a target DNA. Guide RNAs can comprise two segments: a "DNA-targeting segment" and a "protein-binding segment." "Segment" includes a segment, section, or region of a molecule, such as a contiguous stretch of nucleotides in an RNA. Some gRNAs comprise two separate RNA molecules: an "activator-RNA" and a "targeter-RNA." Other gRNAs are a single RNA molecule (single RNA polynucleotide), which can also be called a "single-molecule gRNA," a "single-guide RNA," or an "sgRNA." See, e.g., WO/2013/176772A1, WO/2014/065596A1, WO/2014/089290A1, WO/2014/093622A2, WO/2014/099750A2, WO/2013142578A1, and WO 2014/131833A1, each of which is herein incorporated by reference. The terms "guide RNA" and "gRNA" are inclusive, including both double-molecule gRNAs and single-molecule gRNAs.

An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA" or "scaffold") molecule. A crRNA comprises both the DNA-targeting segment (single-stranded) of the gRNA and a stretch of nucleotides that forms one half of the dsRNA duplex of the protein-binding segment of the gRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA.

The crRNA and the corresponding tracrRNA hybridize to form a gRNA. The crRNA additionally provides the single stranded DNA-targeting segment that hybridizes to a target sequence. If used for modification within a cell, the exact sequence of a given crRNA or tracrRNA molecule can be designed to be specific to the species in which the RNA molecules will be used. See, for example, Mali et al. (2013) *Science* 339:823-826; Jinek et al. (2012) *Science* 337:816-821; Hwang et al. (2013) *Nat. Biotechnol.* 31:227-229; Jiang et al. (2013) *Nat. Biotechnol.* 31:233-239; and Cong et al. (2013) *Science* 339:819-823, each of which is herein incorporated by reference.

The DNA-targeting segment (crRNA) of a given gRNA comprises a nucleotide sequence that is complementary to a sequence in a target DNA. The DNA-targeting segment of a gRNA interacts with a target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the Cas9 system and organism but often contain a targeting segment of between 21 to 72 nucleotides length, flanked by two direct repeats (DR) of a length of between 21 to 46 nucleotides (see, e.g., WO2014/131833). In the case of *S. pyogenes*, the DRs are 36 nucleotides long and the targeting segment is 30 nucleotides long. The 3' located DR is complementary to and hybridizes with the corresponding tracrRNA, which in turn binds to the Cas9 protein.

The DNA-targeting segment can have a length of from about 12 nucleotides to about 100 nucleotides. For example, the DNA-targeting segment can have a length of from about 12 nucleotides (nt) to about 80 nt, from about 12 nt to about 50 nt, from about 12 nt to about 40 nt, from about 12 nt to about 30 nt, from about 12 nt to about 25 nt, from about 12 nt to about 20 nt, or from about 12 nt to about 19 nt. Alternatively, the DNA-targeting segment can have a length of from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 19 nt to about 70 nt, from about 19 nt to about 80 nt, from about 19 nt to about 90 nt, from about 19 nt to about 100 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, from about 20 nt to about 60 nt, from about 20 nt to about 70 nt, from about 20 nt to about 80 nt, from about 20 nt to about 90 nt, or from about 20 nt to about 100 nt.

The nucleotide sequence of the DNA-targeting segment that is complementary to a nucleotide sequence (target sequence) of the target DNA can have a length at least about 12 nt. For example, the DNA-targeting sequence (i.e., the sequence within the DNA-targeting segment that is complementary to a target sequence within the target DNA) can have a length at least about 12 nt, at least about 15 nt, at least about 18 nt, at least about 19 nt, at least about 20 nt, at least about 25 nt, at least about 30 nt, at least about 35 nt, or at least about 40 nt. Alternatively, the DNA-targeting sequence can have a length of from about 12 nucleotides (nt) to about 80 nt, from about 12 nt to about 50 nt, from about 12 nt to about 45 nt, from about 12 nt to about 40 nt, from about 12 nt to about 35 nt, from about 12 nt to about 30 nt, from about 12 nt to about 25 nt, from about 12 nt to about 20 nt, from about 12 nt to about 19 nt, from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some cases, the DNA-targeting sequence can have a length of at about 20 nt.

TracrRNAs can be in any form (e.g., full-length tracrR-NAs or active partial tracrRNAs) and of varying lengths. They can include primary transcripts or processed forms. For example, tracrRNAs (as part of a single-guide RNA or as a separate molecule as part of a two-molecule gRNA) may comprise or consist of all or a portion of a wild-type tracrRNA sequence (e.g., about or more than about 20, 26, 32, 45, 48, 54, 63, 67, 85, or more nucleotides of a wild-type tracrRNA sequence). Examples of wild-type tracrRNA sequences from *S. pyogenes* include 171-nucleotide, 89-nucleotide, 75-nucleotide, and 65-nucleotide versions. See, for example, Deltcheva et al. (2011) Nature 471:602-607; WO 2014/093661, each of which is incorporated herein by reference in their entirety. Examples of tracrRNAs within single-guide RNAs (sgRNAs) include the tracrRNA segments found within +48, +54, +67, and +85 versions of sgRNAs, where "+n" indicates that up to the +n nucleotide of wild-type tracrRNA is included in the sgRNA. See U.S. Pat. No. 8,697,359, incorporated herein by reference in its entirety.

The percent complementarity between the DNA-targeting sequence and the target sequence within the target DNA can be at least 60% (e.g., at least 65%, at least 70%, at least 75%, at least 80%, at least 85%, at least 90%, at least 95%, at least 97%, at least 98%, at least 99%, or 100%). In some cases, the percent complementarity between the DNA-targeting sequence and the target sequence within the target DNA is at least 60% over about 20 contiguous nucleotides. In one example, the percent complementarity between the DNA-targeting sequence and the target sequence within the target DNA is 100% over the 14 contiguous nucleotides at the 5' end of the target sequence within the complementary strand of the target DNA and as low as 0% over the remainder. In such a case, the DNA-targeting sequence can be considered to be 14 nucleotides in length. In another example, the percent complementarity between the DNA-targeting sequence and the target sequence within the target DNA is 100% over the seven contiguous nucleotides at the 5' end of the target sequence within the complementary strand of the target DNA and as low as 0% over the remainder. In such a case, the DNA-targeting sequence can be considered to be 7 nucleotides in length.

The protein-binding segment of a gRNA can comprise two stretches of nucleotides that are complementary to one another. The complementary nucleotides of the protein-binding segment hybridize to form a double stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin)); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, etc.); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. The gRNA can also be provided in the form of DNA encoding the RNA. The DNA encoding the gRNA can encode a single RNA molecule (sgRNA) or separate RNA molecules (e.g., separate crRNA and tracrRNA). In the latter case, the DNA encoding the gRNA can be provided as separate DNA molecules encoding the crRNA and tracrRNA, respectively.

When a DNA encoding a gRNA is introduced into the cell, the gRNA can be transiently, conditionally, or constitutively expressed in the cell. DNAs encoding gRNAs can be stably integrated in the genome of the cell and operably linked to a promoter active in the cell. Alternatively, DNAs encoding gRNAs can be operably linked to a promoter in an expression construct. For example, the DNA encoding the gRNA can be in a targeting vector comprising a nucleic acid insert and/or a vector comprising a nucleic acid encoding a Cas protein. Alternatively, it can be in a vector or a plasmid that is separate from the targeting vector comprising the nucleic acid insert and/or separate from the vector comprising the nucleic acid encoding the Cas protein. Such promoters can be active, for example, in a human iPS cell or a non-pluripotent cell transformed to express a pluripotent state. Such promoters can be, for example, conditional promoters, inducible promoters, constitutive promoters, or tissue-specific promoters. In some instances, the promoter is an RNA polymerase III promoter, such as a human U6 promoter.

Alternatively, gRNAs can be prepared by various other methods. For example, gRNAs can be prepared by in vitro transcription using, for example, T7 RNA polymerase (see, for example, WO 2014/089290 and WO 2014/065596). Guide RNAs can also be a synthetically produced molecule prepared by chemical synthesis.

A target sequence for a CRISPR/Cas system includes nucleic acid sequences present in a target DNA to which a DNA-targeting segment of a gRNA will bind, provided sufficient conditions for binding exist. For example, target sequences include sequences to which a guide RNA is designed to have complementarity, where hybridization between a target sequence and a DNA targeting sequence promotes the formation of a CRISPR complex. Full complementarity is not necessarily required, provided there is sufficient complementarity to cause hybridization and promote formation of a CRISPR complex. Target sequences also include cleavage sites for Cas proteins, described in more detail below. A target sequence can comprise any polynucleotide, which can be located, for example, in the nucleus or cytoplasm of a cell or within an organelle of a cell, such as a mitochondrion or chloroplast.

The target sequence within a target DNA can be targeted by (i.e., be bound by, or hybridize with, or be complementary to) a Cas protein or a gRNA. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001)). The strand of the target DNA that is complementary to and hybridizes with the Cas protein or gRNA can be called the "complementary strand," and the strand of the target DNA that is complementary to the "complementary strand" (and is therefore not complementary to the Cas protein or gRNA) can be called "noncomplementary strand" or "template strand."

The Cas protein can cleave the nucleic acid at a site within or outside of a nucleic acid sequence present in a target DNA to which a DNA-targeting segment of a gRNA will bind. The "cleavage site" includes the position of a nucleic acid at which a Cas protein produces a single-strand break or a double-strand break. For example, formation of a CRISPR complex (comprising a gRNA hybridized to a target sequence and complexed with a Cas protein) can result in cleavage of one or both strands in or near (e.g., within 1, 2, 3, 4, 5, 6, 7, 8, 9, 10, 20, 50, or more base pairs from) the nucleic acid sequence present in a target DNA to which a DNA-targeting segment of a gRNA will bind. If the cleavage site is outside of the nucleic acid sequence present in a target DNA to which a DNA-targeting segment of a gRNA will bind, the cleavage site is still considered to be within the "target sequence." The cleavage site can be on only one strand or on both strands of a nucleic acid. Cleavage sites can be at the same position on both strands of the nucleic acid (producing blunt ends) or can be at different sites on each strand (producing staggered ends). Staggered ends can be produced, for example, by using two Cas proteins which produce a single-strand break at different cleavage sites on each strand. For example, a first nickase can create a single strand break on the first strand of double stranded DNA (dsDNA), while a second nickase can create a single strand break on the second strand of dsDNA such that overhanging sequences are created. In some cases, the target sequence of the nickase on the first strand is separated from the target sequence of the nickase on the second strand by at least 2, 3, 4, 5, 6, 7, 8, 9, 10, 15, 20, 25, 30, 40, 50, 75, 100, 250, 500, or 1,000 base pairs.

Site-specific cleavage of target DNA by Cas9 can occur at locations determined by both (i) base-pairing complementarity between the gRNA and the target DNA and (ii) a short motif, called the protospacer adjacent motif (PAM), in the target DNA. The PAM can flank the target sequence. Optionally, the target sequence can be flanked on the 3' end by the PAM. For example, the cleavage site of Cas9 can be about 1 to about 10 or about 2 to about 5 base pairs (e.g., 3 base pairs) upstream or downstream of the PAM sequence. In some cases (e.g., when Cas9 from *S. pyogenes* or a closely related Cas9 is used), the PAM sequence of the non-complementary strand can be 5'-XGG-3', where X is any DNA nucleotide and is immediately 3' of the target sequence of the non-complementary strand of the target DNA. As such, the PAM sequence of the complementary strand would be 5'-CCY-3', where Y is any DNA nucleotide and is immediately 5' of the target sequence of the complementary strand of the target DNA. In some such cases, X and Y can be complementary and the X-Y base pair can be any base pair (e.g., X=C and Y=G; X=G and Y=C; X=A and Y=T; X=T, and Y=A).

Examples of target sequences include a DNA sequence complementary to the DNA-targeting segment of a gRNA, or such a DNA sequence in addition to a PAM sequence. One example of a target sequence comprises the nucleotide sequence of GNNNNNNNNNNNNNNNNNNNGG ($GN_{1-20}GG$; SEQ ID NO: 2). Other target sequences can have between 4-22 nucleotides in length of SEQ ID NO: 2, including the 5' G and the 3' GG. Yet other target sequences can have between 14 and 20 nucleotides in length of SEQ ID NO: 2.

The target sequence can be any nucleic acid sequence endogenous or exogenous to a cell. The target sequence can be a sequence coding a gene product (e.g., a protein) or a non-coding sequence (e.g., a regulatory sequence or junk DNA) or can include both.

Active variants and fragments of nuclease agents (i.e. an engineered nuclease agent) are also provided. Such active variants can comprise at least 65%, 70%, 75%, 80%, 85%, 90%, 91%, 92%, 93%, 94%, 95%, 96%, 97%, 98%, 99% or more sequence identity to the native nuclease agent, wherein the active variants retain the ability to cut at a desired recognition site and hence retain nick or double-strandbreak-inducing activity. For example, any of the nuclease agents described herein can be modified from a native endonuclease sequence and designed to recognize and induce a nick or double-strand break at a recognition site that was not recognized by the native nuclease agent. Thus, in some embodiments, the engineered nuclease has a specificity to induce a nick or double-strand break at a recognition site that is different from the corresponding native nuclease agent recognition site. Assays for nick or double-strand-break-inducing activity are known and generally measure the overall activity and specificity of the endonuclease on DNA substrates containing the recognition site.

The nuclease agent may be introduced into the pluripotent cell by any means known in the art. The polypeptide encoding the nuclease agent may be directly introduced into the cell. Alternatively, a polynucleotide encoding the nuclease agent can be introduced into the cell. When a polynucleotide encoding the nuclease agent is introduced into the cell, the nuclease agent can be transiently, conditionally or constitutively expressed within the cell. Thus, the polynucleotide encoding the nuclease agent can be contained in an expression cassette and be operably linked to a conditional promoter, an inducible promoter, a constitutive promoter, or a tissue-specific promoter. Alternatively, the nuclease agent is introduced into the cell as an mRNA encoding a nuclease agent.

In specific embodiments, the polynucleotide encoding the nuclease agent is stably integrated in the genome of the pluripotent cell and operably linked to a promoter active in the cell. In other embodiments, the polynucleotide encoding the nuclease agent is in the same targeting vector comprising the nucleic acid insert, while in other instances the polynucleotide encoding the nuclease agent is in a vector or a plasmid that is separate from the targeting vector comprising the nucleic acid insert.

When the nuclease agent is provided to the pluripotent cell through the introduction of a polynucleotide encoding the nuclease agent, such a polynucleotide encoding a nuclease agent can be modified to substitute codons having a higher frequency of usage in the cell of interest, as compared to the naturally occurring polynucleotide sequence encoding the nuclease agent. For example the polynucleotide encoding the nuclease agent can be modified to substitute codons having a higher frequency of usage in a human cell, as compared to the naturally occurring polynucleotide sequence.

b. Selection Markers

Various selection markers can be used in the methods and compositions disclosed herein which provide for modifying a target genomic locus on a chromosome. Such markers are disclosed elsewhere herein and include, but are not limited to, selection markers that impart resistance to an antibiotic such as G418, hygromycin, blasticidin, neomycin, or puromycin. The polynucleotide encoding the selection markers are operably linked to a promoter active in a human iPS cell or a non-pluripotent cell transformed to express a naïve state.

c. Target Genomic Locus

Various methods and compositions are provided which allow for the integration of at least one nucleic acid insert at a target genomic locus on a chromosome. A "target genomic locus on a chromosome" comprises any segment or region of DNA on a chromosome that one desires to integrate a nucleic acid insert. The genomic locus on a chromosome being targeted can be native to human iPS cell or a non-pluripotent cell transformed to express a pluripotent state, or alternatively can comprise a heterologous or exogenous segment of DNA that was integrated into a chromosome of the cell. Such heterologous or exogenous segments of DNA can include transgenes, expression cassettes, polynucleotide encoding selection makers, or heterologous or exogenous regions of genomic DNA. The target genomic locus on the chromosome can comprise any of the targeted genomic integration system including, for example, the recognition site, the selection marker, previously integrated nucleic acid inserts, polynucleotides encoding nuclease agents, promoters, etc. Alternatively, the target genomic locus on the chromosome can be located within a yeast artificial chromosome (YAC), bacterial artificial chromosome (BAC), a human artificial chromosome, or any other engineered genomic region contained in an appropriate host cell. Thus, in specific embodiments, the targeted genomic locus on the chromosome can comprise native genomic sequence from a human cell or heterologous or exogenous genomic nucleic acid sequence from a non-human mammal, a non-human cell, a rodent, a human, a rat, a mouse, a hamster, a rabbit, a pig, a bovine, a deer, a sheep, a goat, a chicken, a cat, a dog, a ferret, a primate (e.g., marmoset, rhesus monkey), domesticated mammal or an agricultural mammal, or any other organism of interest or a combination thereof.

d. Targeting Vectors and Nucleic Acid Inserts

As outlined above, methods and compositions provided herein employ targeting vectors alone or in combination with a nuclease agent. "Homologous recombination" is used conventionally to refer to the exchange of DNA fragments between two DNA molecules at cross-over sites within the regions of homology.

i. Nucleic Acid Insert

One or more separate nucleic acid inserts can be employed in the methods disclosed herein, and they can be introduced into a cell via separate targeting vectors or on the same targeting vector. Nucleic acid inserts include segments of DNA to be integrated at genomic target loci. Integration of a nucleic acid insert at a target locus can result in addition of a nucleic acid sequence of interest to the target locus, deletion of a nucleic acid sequence of interest at the target locus, and/or replacement of a nucleic acid sequence of interest at the target locus.

The nucleic acid insert or the corresponding nucleic acid at the target locus being replaced can be a coding region, an intron, an exon, an untranslated region, a regulatory region, a promoter, an enhancer, or any combination thereof. Moreover, the nucleic acid insert or the corresponding nucleic acid at the target locus being replaced can be of any desired length, including, for example, between 10-100 nucleotides in length, 100-500 nucleotides in length, 500 nucleotides-1 kb in length, 1 kb to 1.5 kb nucleotide in length, 1.5 kb to 2 kb nucleotides in length, 2 kb to 2.5 kb nucleotides in length, 2.5 kb to 3 kb nucleotides in length, 3 kb to 5 kb nucleotides in length, 5 kb to 8 kb nucleotides in length, 8 kb to 10 kb nucleotides in length or more. In other cases, the length can be from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, from about 350 kb to about 400 kb, from about 400 kb to about 800 kb, from about 800 kb to 1 Mb, from about 1 Mb to about 1.5 Mb, from about 1.5 Mb to about 2 Mb, from about 2 Mb, to about 2.5 Mb, from about 2.5 Mb to about 2.8 Mb, from about 2.8 Mb to about 3 Mb. In yet other cases, the length can be at least 100, 200, 300, 400, 500, 600, 700, 800, or 900 nucleotides or at least 1 kb, 2 kb, 3 kb, 4 kb, 5 kb, 6 kb, 7 kb, 8 kb, 9 kb, 10 kb, 11 kb, 12 kb, 13 kb, 14 kb, 15 kb, 16 kb or greater.

In some targeting vectors, the nucleic acid insert can be from about 5 kb to about 200 kb, from about 5 kb to about 10 kb, from about 10 kb to about 20 kb, from about 20 kb to about 30 kb, from about 30 kb to about 40 kb, from about 40 kb to about 50 kb, from about 60 kb to about 70 kb, from about 80 kb to about 90 kb, from about 90 kb to about 100 kb, from about 100 kb to about 110 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, from about 190 kb to about 200 kb. Alternatively, the nucleic acid insert can be from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb.

In some cases, the replacement of the nucleic acid at the target locus results in the deletion of a target sequence ranging from about 1 kb to about 200 kb, from about 2 kb to about 20 kb, or from about 0.5 kb to about 3 Mb. In some cases, the extent of the deletion is greater than a total length of the 5' homology arm and the 3' homology arm.

In some cases, the extent of the deletion of the target sequence ranges from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 20 kb to about 30 kb, from about 30 kb to about 40 kb, from about 40 kb to about 50 kb, from about 50 kb to about 60 kb, from about 60 kb to about 70 kb, from about 70 kb to about 80 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, from about 190 kb to about 200 kb, from about 200 kb to about 250 kb, from about 250 kb to about 300 kb, from about 300 kb to about 350 kb, from about 350 kb to about 400 kb, from about 400 kb to about 800 kb, from about 800 kb to 1 Mb, from about 1 Mb to about 1.5 Mb, from about 1.5 Mb to about 2 Mb, from about 2 Mb, to about 2.5 Mb, from about 2.5 Mb to about 2.8 Mb, from about 2.8 Mb to about 3 Mb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb.

In other cases, the nucleic acid insert or the corresponding nucleic acid at the target locus being replaced can be at least 10 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, at least 300 kb, at least 350 kb, at least 400 kb, at least 450 kb, or at least 500 kb or greater.

The nucleic acid insert can comprise genomic DNA or any other type of DNA. For example, the nucleic acid insert can be from a prokaryote, a eukaryote, a yeast, a bird (e.g., chicken), a non-human mammal, a rodent, a human, a rat, a mouse, a hamster a rabbit, a pig, a bovine, a deer, a sheep, a goat, a cat, a dog, a ferret, a primate (e.g., marmoset, rhesus monkey), a domesticated mammal, an agricultural mammal, or any other organism of interest. In one example, the insert polynucleotide can comprise any human or non-human genomic locus.

The nucleic acid insert and/or the nucleic acid at the target locus can comprise a coding sequence or a non-coding sequence, such as a regulatory element (e.g., a promoter, an enhancer, or a transcriptional repressor-binding element). For example, the nucleic acid insert can comprise a knock-in allele of at least one exon of an endogenous gene, or a knock-in allele of the entire endogenous gene (i.e., "gene-swap knock-in").

The nucleic acid insert can also comprise a conditional allele. The conditional allele can be a multifunctional allele, as described in US 2011/0104799, which is incorporated by reference in its entirety. For example, the conditional allele can comprise: (a) an actuating sequence in sense orientation with respect to transcription of a target gene; (b) a drug selection cassette (DSC) in sense or antisense orientation; (c) a nucleotide sequence of interest (NSI) in antisense orientation; and (d) a conditional by inversion module (COIN, which utilizes an exon-splitting intron and an invertible gene-trap-like module) in reverse orientation. See, for example, US 2011/0104799, which is incorporated by reference in its entirety. The conditional allele can further comprise recombinable units that recombine upon exposure to a first recombinase to form a conditional allele that (i) lacks the actuating sequence and the DSC; and (ii) contains the NSI in sense orientation and the COIN in antisense orientation. See US 2011/0104799.

Some nucleic acid inserts comprise a polynucleotide encoding a selection marker. The selection marker can be contained in a selection cassette. Such selection markers include, but are not limited, to neomycin phosphotransferase (neon), hygromycin B phosphotransferase (hygr), puromycin-N-acetyltransferase (puror), blasticidin S deaminase (bsrr), xanthine/guanine phosphoribosyl transferase (gpt), or herpes simplex virus thymidine kinase (HSV-k), or a combination thereof. The polynucleotide encoding the selection marker can be operably linked to a promoter active in a cell being targeted.

In some targeting vectors, the nucleic acid insert comprises a reporter gene. Examples of reporter genes are genes encoding luciferase, β-galactosidase, green fluorescent protein (GFP), enhanced green fluorescent protein (eGFP), cyan fluorescent protein (CFP), yellow fluorescent protein (YFP), enhanced yellow fluorescent protein (eYFP), blue fluorescent protein (BFP), enhanced blue fluorescent protein (eBFP), DsRed, ZsGreen, MmGFP, mPlum, mCherry, tdTomato, mStrawberry, J-Red, mOrange, mKO, mCitrine, Venus, YPet, Emerald, CyPet, Cerulean, T-Sapphire, alkaline phosphatase, and a combination thereof. Such reporter genes can be operably linked to a promoter active in a cell being targeted.

In some targeting vectors, the nucleic acid insert comprises one or more expression cassettes or deletion cassettes. A given cassette can comprise a nucleotide sequence of interest, a nucleic acid encoding a selection marker, and/or a reporter gene, along with various regulatory components that influence expression. Examples of selectable markers and reporter genes that can be included are discussed in detail elsewhere herein.

In some targeting vectors, the insert nucleic acid comprises a nucleic acid flanked with site-specific recombination target sequences. Although the entire insert nucleic acid can be flanked by such site-specific recombination target sequences, any region or individual polynucleotide of interest within the insert nucleic acid can also be flanked by such sites. Site-specific recombination target sequences, which can flank the insert nucleic acid or any polynucleotide of interest in the insert nucleic acid can include, for example, loxP, lox511, lox2272, lox66, lox71, loxM2, lox5171, FRT, FRT11, FRT71, attp, att, FRT, rox, and a combination thereof. In one example, the site-specific recombination sites flank a polynucleotide encoding a selection marker and/or a reporter gene contained within the insert nucleic acid. Following integration of the insert nucleic acid at a targeted locus, the sequences between the site-specific recombination sites can be removed.

ii. Targeting Vectors

Targeting vectors can be employed to introduce the nucleic acid insert into a target genomic locus and comprise the nucleic acid insert and homology arms that flank the nucleic acid insert. Targeting vectors can be in linear form or in circular form, and can be single-stranded or double-stranded. For ease of reference, the homology arms are referred to herein as 5' and 3' (i.e., upstream and downstream) homology arms. This terminology relates to the relative position of the homology arms to the nucleic acid insert within the targeting vector. The 5' and 3' homology arms correspond to regions within the targeted locus, which are referred to herein as "5' target sequence" and "3' target sequence," respectively.

A homology arm and a target sequence "correspond" or are "corresponding" to one another when the two regions share a sufficient level of sequence identity to one another to act as substrates for a homologous recombination reaction. The term "homology" includes DNA sequences that are either identical or share sequence identity to a corresponding sequence. The sequence identity between a given target sequence and the corresponding homology arm found on the targeting vector can be any degree of sequence identity that allows for homologous recombination to occur. For example, the amount of sequence identity shared by the homology arm of the targeting vector (or a fragment thereof) and the target sequence (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a corresponding region of homology between the homology arm and the corresponding target sequence can be of any length that is sufficient to promote homologous recombination at the cleaved recognition site. For example, a given homology arm and/or corresponding target sequence can comprise corresponding regions of homology that are at least about 5-10 kb, 5-15 kb, 5-20 kb, 5-25 kb, 5-30 kb, 5-35 kb, 5-40 kb, 5-45 kb, 5-50 kb, 5-55 kb, 5-60 kb, 5-65 kb, 5-70 kb, 5-75 kb, 5-80 kb, 5-85 kb, 5-90 kb, 5-95 kb, 5-100 kb, 100-200 kb, or 200-300 kb in length or more (such as described in the LTVEC vectors described elsewhere herein) such that the homology arm has sufficient homology to undergo homologous recombination with the corresponding target sequences within the genome of the cell.

The homology arms can correspond to a locus that is native to a cell (e.g., the targeted locus), or alternatively they can correspond to a region of a heterologous or exogenous segment of DNA that was integrated into the genome of the cell, including, for example, transgenes, expression cassettes, or heterologous or exogenous regions of DNA. Alternatively, the homology arms of the targeting vector can correspond to a region of a yeast artificial chromosome (YAC), a bacterial artificial chromosome (BAC), a human artificial chromosome, or any other engineered region contained in an appropriate host cell. Still further, the homology arms of the targeting vector can correspond to or be derived from a region of a BAC library, a cosmid library, or a P1 phage library. In certain instances, the homology arms of the targeting vector correspond to a locus that is native, heterologous, or exogenous to a human iPS cell or a non-pluripotent cell transformed to express a naïve state. In some cases, the homology arms correspond to a locus of the cell that is not targetable using a conventional method or that can be targeted only incorrectly or only with significantly low efficiency in the absence of a nick or double-strand break induced by a nuclease agent (e.g., a Cas protein). In some cases, the homology arms are derived from synthetic DNA.

In some targeting vectors, the 5' and 3' homology arms correspond to a safe harbor locus. Interactions between integrated exogenous DNA and a host genome can limit the reliability and safety of integration and can lead to overt phenotypic effects that are not due to the targeted genetic modification but are instead due to unintended effects of the integration on surrounding endogenous genes. For example, randomly inserted transgenes can be subject to position effects and silencing, making their expression unreliable and unpredictable. Likewise, integration of exogenous DNA into a chromosomal locus can affect surrounding endogenous genes and chromatin, thereby altering cell behavior and phenotypes. Safe harbor loci include chromosomal loci where transgenes or other exogenous nucleic acid inserts can be stably and reliably expressed in all tissues of interest without overtly altering cell behavior or phenotype. See, e.g., Sadelain et al. (2012) Nat. Rev. Cancer 12:51-58. For example, safe harbor loci can include chromosomal loci where exogenous DNA can integrate and function in a predictable manner without adversely affecting endogenous gene structure or expression. Safe harbor loci can include extragenic regions or intragenic regions such as, for example, loci within genes that are non-essential, dispensable, or able to be disrupted without overt phenotypic consequences.

For example, the Rosa26 locus and its equivalent in humans offer an open chromatin configuration in all tissues and is ubiquitously expressed during embryonic development and in adults. See Zambrowicz et al. (1997) Proc. Natl. Acad. Sci. USA 94:3789-3794. In addition, the Rosa26 locus can be targeted with high efficiency, and disruption of the Rosa26 gene produces no overt phenotype. Another example of a suitable locus is the Ch25h locus.

A homology arm of a targeting vector can be of any length that is sufficient to promote a homologous recombination event with a corresponding target sequence, including, for example, at least 5-10 kb, 5-15 kb, 5-20 kb, 5-25 kb, 5-30 kb, 5-35 kb, 5-40 kb, 5-45 kb, 5-50 kb, 5-55 kb, 5-60 kb, 5-65 kb, 5-70 kb, 5-75 kb, 5-80 kb, 5-85 kb, 5-90 kb, 5-95 kb, 5-100 kb, 100-200 kb, or 200-300 kb in length or greater. As described in further detail below, large targeting vectors can employ targeting arms of greater length.

Nuclease agents (e.g., CRISPR/Cas systems) can be employed in combination with targeting vectors to aid in the modification of a target locus. Such nuclease agents may promote homologous recombination between the targeting vector and the target locus. When nuclease agents are employed in combination with a targeting vector, the targeting vector can comprise 5' and 3' homology arms corresponding to 5' and 3' target sequences located in sufficient proximity to a nuclease cleavage site so as to promote the occurrence of a homologous recombination event between the target sequences and the homology arms upon a nick or double-strand break at the nuclease cleavage site. The term "nuclease cleavage site" includes a DNA sequence at which a nick or double-strand break is created by a nuclease agent (e.g., a Cas9 cleavage site). The target sequences within the targeted locus that correspond to the 5' and 3' homology arms of the targeting vector are "located in sufficient proximity" to a nuclease cleavage site if the distance is such as to promote the occurrence of a homologous recombination event between the 5' and 3' target sequences and the homology arms upon a nick or double-strand break at the recognition site. Thus, in specific instances, the target sequences corresponding to the 5' and/or 3' homology arms of the targeting vector are within at least 1 nucleotide of a given recognition site or are within at least 10 nucleotides to about 14 kb of a given recognition site. In some cases, the nuclease cleavage site is immediately adjacent to at least one or both of the target sequences.

The spatial relationship of the target sequences that correspond to the homology arms of the targeting vector and the nuclease cleavage site can vary. For example, target sequences can be located 5' to the nuclease cleavage site, target sequences can be located 3' to the recognition site, or the target sequences can flank the nuclease cleavage site.

Combined use of the targeting vector (including, for example, a large targeting vector) with a nuclease agent can result in an increased targeting efficiency compared to use of the targeting vector alone. For example, when a targeting vector is used in conjunction with a nuclease agent, targeting efficiency of the targeting vector can be increased by at least two-fold, at least three-fold, at least 4-fold, or at least 10-fold when compared to use of the targeting vector alone.

iii. Large Targeting Vectors

Some targeting vectors are "large targeting vectors" or "LTVECs," which includes targeting vectors that comprise homology arms that correspond to and are derived from nucleic acid sequences larger than those typically used by other approaches intended to perform homologous recombination in cells. Examples of generating targeted genetic modifications using LTVECs are disclosed, for example, in WO 2015/088643, US 2015/0159175, US 2015/0159174, US 2014/0310828, US 2014/0309487, and US 2013-0309670, each of which is herein incorporated by reference in its entirety for all purposes. LTVECs also include targeting vectors comprising nucleic acid inserts having nucleic acid sequences larger than those typically used by other approaches intended to perform homologous recombination in cells. For example, LTVECs make possible the modification of large loci that cannot be accommodated by traditional plasmid-based targeting vectors because of their size limitations. For example, the targeted locus can be (i.e., the 5' and 3' homology arms can correspond to) a locus of the cell that is not targetable using a conventional method or that can be targeted only incorrectly or only with significantly low efficiency in the absence of a nick or double-strand break induced by a nuclease agent (e.g., a Cas protein).

Examples of LTVECs include vectors derived from a bacterial artificial chromosome (BAC), a human artificial chromosome, or a yeast artificial chromosome (YAC). Non-limiting examples of LTVECs and methods for making them are described, e.g., in U.S. Pat. Nos. 6,586,251; 6,596,541; 7,105,348; and WO 2002/036789 (PCT/US01/45375), each of which is herein incorporated by reference. LTVECs can be in linear form or in circular form.

LTVECs can be of any length, including, for example, from about 50 kb to about 300 kb, from about 50 kb to about 75 kb, from about 75 kb to about 100 kb, from about 100 kb to 125 kb, from about 125 kb to about 150 kb, from about 150 kb to about 175 kb, about 175 kb to about 200 kb, from about 200 kb to about 225 kb, from about 225 kb to about 250 kb, from about 250 kb to about 275 kb or from about 275 kb to about 300 kb. Alternatively, an LTVEC can be at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, at least 300 kb, at least 350 kb, at least 400 kb, at least 450 kb, or at least 500 kb or greater. The size of an LTVEC can be too large to enable screening of targeting events by conventional assays, e.g., southern blotting and long-range (e.g., 1 kb to 5 kb) PCR.

In some cases, an LTVEC comprises a nucleic acid insert ranging from about 5 kb to about 200 kb, from about 5 kb to about 10 kb, from about 10 kb to about 20 kb, from about 20 kb to about 30 kb, from about 30 kb to about 40 kb, from about 40 kb to about 50 kb, from about 60 kb to about 70 kb, from about 80 kb to about 90 kb, from about 90 kb to about 100 kb, from about 100 kb to about 110 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb. In other cases, the insert nucleic acid can range from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb.

In some LTVECs, the sum total of the upstream homology arm and the downstream homology arm is at least 10 kb. In other LTVECs, the upstream homology arm ranges from about 5 kb to about 100 kb and/or the downstream homology arm ranges from about 5 kb to about 100 kb. The sum total of the upstream and downstream homology arms can be, for example, from about 5 kb to about 10 kb, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 70 kb to about 80 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb.

In some cases, the LTVEC and nucleic acid insert are designed to allow for a deletion at the target locus from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb. Alternatively, the deletion can be at least 10 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, at least 300 kb, at least 350 kb, at least 400 kb, at least 450 kb, or at least 500 kb or greater.

In other cases, the LTVEC and nucleic acid insert are designed to allow for an insertion into the target locus of an exogenous nucleic acid sequence ranging from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb. Alternatively, the insertion can be at least 10 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, at least 300 kb, at least 350 kb, at least 400 kb, at least 450 kb, or at least 500 kb or greater.

In yet other cases, the nucleic acid insert and/or the region of the endogenous locus being deleted is at least 100, 200, 300, 400, 500, 600, 700, 800, or 900 nucleotides or at least 1 kb, 2 kb, 3 kb, 4 kb, 5 kb, 6 kb, 7 kb, 8 kb, 9 kb, 10 kb, 11 kb, 12 kb, 13 kb, 14 kb, 15 kb, 16 kb or greater.

iv. Methods of Integrating a Nucleic acid insert Near the Recognition Site on a Chromosome by Homologous Recombination In some examples, methods for modifying a target genomic locus on a chromosome in a pluripotent cell can comprise: (a) providing a cell comprising a target genomic locus on a chromosome, (b) introducing into the cell a first targeting vector comprising a first nucleic acid insert flanked by 5' and 3' homology arms corresponding to 5' and 3' target sequences; and (c) identifying at least one cell comprising in its genome the first nucleic acid insert integrated at the target genomic locus on the chromosome. As discussed in detail elsewhere herein, in specific embodiments, the sum total of the first homology arm and the second homology arm of the targeting vector is about 4 kb, 5 kb, 6 kb, 7 kb, 8 kb, 9 kb, about 4 kb to about 5 kb, about 5 kb to about 6 kb, about 6 kb to about 7 kb, about 8 kb to about 9 kb, or is at least 10 kb or at least 10 kb and less than 150 kb. In specific embodiments, an LTVEC is employed. In one non-limiting embodiment, such methods are performed employing the culture medium provided herein.

In other examples, methods for modifying a target genomic locus on a chromosome in a pluripotent cell can comprise: (a) providing a cell comprising a target genomic locus on a chromosome comprising a recognition site for a nuclease agent, (b) introducing into the cell (i) the nuclease agent, wherein the nuclease agent induces a nick or double-strand break at the first recognition site; and, (ii) a first targeting vector comprising a first nucleic acid insert flanked by 5' and 3' homology arms corresponding to 5' and 3' target sequences located in sufficient proximity to the first recognition site; and (c) identifying at least one cell comprising in its genome the first nucleic acid insert integrated at the target genomic locus on the chromosome. As discussed in detail elsewhere herein, in specific embodiments, the sum total of the first homology arm and the second homology arm of the targeting vector is about 4 kb, 5 kb, 6 kb, 7 kb, 8 kb, 9 kb, about 4 kb to about 5 kb, about 5 kb to about 6 kb, about 6 kb to about 7 kb, about 8 kb to about 9 kb, or is at least 10 kb or at least 10 kb and less than 150 kb. In specific embodiments, an LTVEC is employed. In one non-limiting embodiment, such methods are performed employing the culture medium provided herein.

Various methods can also be employed to identify pluripotent cells having the nucleic acid insert integrated at the genomic target locus. Insertion of the nucleic acid insert at the genomic target locus results in a "modification of allele." The term "modification of allele" or "MOA" includes the modification of the exact DNA sequence of one allele of a gene(s) or chromosomal locus (loci) in a genome. Examples of "modification of allele (MOA)" include, but are not limited to, deletions, substitutions, or insertions of as little as a single nucleotide or deletions of many kilobases spanning a gene(s) or chromosomal locus (loci) of interest, as well as any and all possible modifications between these two extremes.

In various embodiments, to facilitate identification of the targeted modification, a high-throughput quantitative assay, namely, modification of allele (MOA) assay, is employed. The MOA assay described herein allows a large-scale screening of a modified allele(s) in a parental chromosome following a genetic modification. The MOA assay can be carried out via various analytical techniques, including, but not limited to, a quantitative PCR, e.g., a real-time PCR (qPCR). For example, the real-time PCR comprises a first primer-probe set that recognizes the target locus and a second primer-probe set that recognizes a non-targeted reference locus. In addition, the primer-probe set comprises a fluorescent probe that recognizes the amplified sequence. The quantitative assay can also be carried out via a variety of analytical techniques, including, but not limited to, fluorescence-mediated in situ hybridization (FISH), comparative genomic hybridization, isothermic DNA amplification, quantitative hybridization to an immobilized probe(s), Invader Probes®, MMP Assays®, TaqMan® Molecular Beacon, and Eclipse™ probe technology. See, for example, US2005/0144655, incorporated by reference herein in its entirety.

In various embodiments, in the presence of the nick or double strand break, targeting efficiency of a targeting vector (such as a LTVEC) at the target genomic locus is at least about 2-fold higher, at least about 3-fold higher, at least about 4-fold higher than in the absence of the nick or double-strand break (using, e.g., the same targeting vector and the same homology arms and corresponding target sites at the genomic locus of interest but in the absence of an added nuclease agent that makes the nick or double strand break).

The various methods set forth above can be sequentially repeated to allow for the targeted integration of any number of nucleic acid inserts into a given targeted genomic locus on a chromosome. Thus, the various methods provide for the insertion of at least 1, 2, 3, 4, 5, 6, 7, 8, 9, 10, 11, 12, 13, 14, 15, 16, 17, 18, 19, 20 or more nucleic acid inserts into the target genomic locus on a chromosome. In particular embodiments, such sequential tiling methods allow for the reconstruction of large genomic regions from an animal cell or from a mammalian cell (i.e., a human, a non-human, a rodent, a mouse, a monkey, a rat, a hamster, a domesticated mammal or an agricultural animal) into a targeted genomic locus on a chromosome. In such instances, the transfer and reconstruction of genomic regions that include both coding and non-coding regions allow for the complexity of a given region to be preserved by retaining, at least in part, the coding regions, the non-coding regions and the copy number variations found within the native genomic region. Thus, the various methods provide, for example, methods to generate "heterologous" or "exogenous" genomic regions within a human iPS cell or a non-pluripotent cell transformed to express a pluripotent state.

v. Polynucleotides of Interest

Any polynucleotide of interest may be contained in the various nucleic acid inserts and thereby integrated at the target genomic locus on a chromosome. The methods disclosed herein, provide for at least 1, 2, 3, 4, 5, 6 or more polynucleotides of interest to be integrated into the targeted genomic locus.

The polynucleotide of interest within the nucleic acid insert when integrated at the target genomic locus on a chromosome can introduce one or more genetic modifications into the pluripotent cell. The genetic modification can comprise a deletion of an endogenous nucleic acid sequence and/or the addition of an exogenous or heterologous or orthologous polynucleotide into the target genomic locus. In one embodiment, the genetic modification comprises a replacement of an endogenous nucleic acid sequence with an exogenous polynucleotide of interest at the target genomic locus. Thus, methods provided herein allow for the generation of a genetic modification comprising a knockout, a deletion, an insertion, a replacement ("knock-in"), a point mutation, a domain swap, an exon swap, an intron swap, a regulatory sequence swap, a gene swap, or a combination thereof in a target genomic locus on a chromosome. Such modifications may occur upon integration of the first, second, third, fourth, fifth, six, seventh, or any subsequent nucleic acid inserts into the target genomic locus.

The polynucleotide of interest within the nucleic acid insert and/or integrated at the target genomic locus can comprise a sequence that is native or homologous to the pluripotent cell it is introduced into; the polynucleotide of interest can be heterologous to the cell it is introduced to; the polynucleotide of interest can be exogenous to the cell it is introduced into; the polynucleotide of interest can be orthologous to the cell it is introduced into; or the polynucleotide of interest can be from a different species than the cell it is introduced into. "Homologous" in reference to a sequence includes a sequence that is native to the cell. "Heterologous" in reference to a sequence includes a sequence that originates from a foreign species, or, if from the same species, is substantially modified from its native form in composition and/or genomic locus by deliberate human intervention. "Exogenous" in reference to a sequence includes a sequence that originates from a foreign species. "Orthologous" includes a polynucleotide from one species that is functionally equivalent to a known reference sequence in another species (i.e., a species variant). The polynucleotide of interest can be from any organism of interest including, but not limited to, non-human, a rodent, a hamster, a mouse, a rat, a human, a monkey, an avian, an agricultural mammal or a non-agricultural mammal. The polynucleotide of interest can further comprise a coding region, a non-coding region, a regulatory region, or a genomic DNA. Thus, the $1^{st}$, $2^{nd}$, $3^{rd}$, $4^{th}$, $5^{th}$, $6^{th}$, $7^{th}$, and/or any of the subsequent nucleic acid inserts can comprise such sequences.

In one embodiment, the polynucleotide of interest within the nucleic acid insert and/or integrated at the target genomic locus on a chromosome is homologous to a human nucleic acid. In still further embodiments, the polynucleotide of interest integrated at the target locus is a fragment of a genomic nucleic acid. In one embodiment, the genomic nucleic acid is a mouse genomic nucleic acid, a human genomic nucleic acid, a non-human nucleic acid, a rodent nucleic acid, a rat nucleic acid, a hamster nucleic acid, a monkey nucleic acid, an agricultural mammal nucleic acid or a non-agricultural mammal nucleic acid or a combination thereof.

In one embodiment, the polynucleotide of interest can range from about 500 nucleotides to about 200 kb as described above. The polynucleotide of interest can be from about 500 nucleotides to about 5 kb, from about 5 kb to about 200 kb, from about 5 kb to about 10 kb, from about 10 kb to about 20 kb, from about 20 kb to about 30 kb, from about 30 kb to about 40 kb, from about 40 kb to about 50 kb, from about 60 kb to about 70 kb, from about 80 kb to about 90 kb, from about 90 kb to about 100 kb, from about 100 kb to about 110 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb.

The polynucleotide of interest within the nucleic acid insert and/or inserted at the target genomic locus on a chromosome can encode a polypeptide, can encode an miRNA, can encode a long non-coding RNA, or it can comprise any regulatory regions or non-coding regions of interest including, for example, a regulatory sequence, a promoter sequence, an enhancer sequence, a transcriptional repressor-binding sequence, or a deletion of a non-protein-coding sequence, but does not comprise a deletion of a protein-coding sequence. In addition, the polynucleotide of interest within the nucleic acid insert and/or inserted at the target genomic locus on a chromosome can encode a protein expressed in the nervous system, the skeletal system, the digestive system, the circulatory system, the muscular system, the respiratory system, the cardiovascular system, the lymphatic system, the endocrine system, the urinary system, the reproductive system, or a combination thereof.

The polynucleotide of interest within the nucleic acid insert and/or integrated at the target genomic locus on a chromosome can comprises a genetic modification in a coding sequence. Such genetic modifications include, but are not limited to, a deletion mutation of a coding sequence or the fusion of two coding sequences.

The polynucleotide of interest within the nucleic acid insert and/or integrated at the target genomic locus on a chromosome can comprise a polynucleotide encoding a mutant protein. In one embodiment, the mutant protein is characterized by an altered binding characteristic, altered localization, altered expression, and/or altered expression pattern. In one embodiment, the polynucleotide of interest within the nucleic acid insert and/or integrated at the genomic target locus on a chromosome comprises at least one disease allele. In such instances, the disease allele can be a dominant allele or the disease allele is a recessive allele. Moreover, the disease allele can comprise a single nucleotide polymorphism (SNP) allele. The polynucleotide of interest encoding the mutant protein can be from any organism, including, but not limited to, a mammal, a non-human mammal, rodent, mouse, rat, a human, a monkey, an agricultural mammal or a domestic mammal polynucleotide encoding a mutant protein.

The polynucleotide of interest within the nucleic acid insert and/or integrated at the target genomic locus on a chromosome can also comprise a regulatory sequence, including for example, a promoter sequence, an enhancer sequence, a transcriptional repressor-binding sequence, or a transcriptional terminator sequence. In specific embodiments, the polynucleotide of interest within the nucleic acid insert and/or integrated at the target genomic locus on a chromosome comprises a polynucleotide having a deletion of a non-protein-coding sequence, but does not comprise a deletion of a protein-coding sequence. In one embodiment, the deletion of the non-protein-coding sequence comprises a deletion of a regulatory sequence. In another embodiment, the deletion of the regulatory element comprises a deletion of a promoter sequence. In one embodiment, the deletion of the regulatory element comprises a deletion of an enhancer sequence. Such a polynucleotide of interest can be from any organism, including, but not limited to, a mammal, a non-human mammal, rodent, mouse, rat, a human, a monkey, an agricultural mammal or a domestic mammal polynucleotide encoding a mutant protein.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Many modifications and other embodiments of the methods and compositions set forth herein will come to mind to one skilled in the art to which this methods and compositions pertains having the benefit of the teachings presented in the foregoing descriptions and the associated drawings. Therefore, it is to be understood that the methods and compositions are not to be limited to the specific embodiments disclosed and that modifications and other embodiments are included within the scope of the appended claims. Although specific terms are employed herein, they are used in a generic and descriptive sense only and not for purposes of limitation.

The described invention may be embodied in other specific forms without departing from the spirit or essential attributes thereof and, accordingly, reference should be made to the appended claims, rather than to the foregoing specification, as indicating the scope of the invention.

The following examples are offered by way of illustration and not by way of limitation.

EXAMPLES

Example 1. Generation of Human iPS Cells

This example describes the generation of human iPS cells from non-pluripotent human cells. A sample protocol is shown in Table 2. PiggyBac (System Biosciences) vectors (PB-600A_CAGGGS Bst XI (0.64 μg/μL) and PB-200 (0.99 μg/μL) comprising the genes that encode four reprogramming factors (hOct4, hSox2, hKLF-4, hMYC) operably linked to a CM7 promoter were introduced into neonatal human foreskin fibroblasts using RED and BLUE GeneIn™ transfection reagents (GlobalStem). The transfected cells were incubated on NuFF1 feeder cells in E7 medium (Life Technologies) to allow for incorporation of the vectors and expression of the reprogramming factors. E7 medium comprised DMEM/F-12, NaHCO$_3$, L-ascorbic acid, insulin, transferrin, selenium, and FGF-2.

Puromycin selection began 10 days after transfection using 2 μg/mL puromycin in E7 medium. At day 21, colonies were selected and cultured in mTeSR™ medium (mTeSR™ 1 medium from STEMCELL Technologies), which comprised DMEM/F-12, NaHCO$_3$, L-ascorbic acid, insulin, transferrin, selenium, FGF-2, TGF-β1, glutathione, L-glutamine, defined lipids, thiamine, trace elements B and C, β-mercaptoethanol, bovine serum albumin, pipecolic acid, lithium chloride, and GABA. A comparison of the mTeSR™ medium and E7 medium components is shown in Table 3. At days 29 to 57, cells were propagated and passaged in mTeSR™ medium until reaching ~50% confluent in 6 well plates. At days 65 to 73, propagation and passage continued using mTeSR™ medium and Gentle Cell Dissociation Reagent (Stem Cell Technologies). At day 76, medium was changed to low osmolality VG2i medium for further propagation, passage, and maintenance of the cells comprising naïve or naïve-looking hiPSCs. The timing of passage in the above method was determined by cell morphology.

TABLE 2

Sample protocol for generation of human iPS cells.

| Day | Action | Medium |
|---|---|---|
| 0 | Plate NuFF1 cells in 6-well plates (1 × 10$^5$ per well) | Fibroblast medium |
| 1 | piggyBac transfection | E7 Medium |
| 10 | Start puromycin selection (2 ug/mL) | |
| 21 | Pick up colonies by cutting | mTeSR |
| 29-57 | Passage cells until reach ~50% of well (passage by Gentle Cell Dissociation Reagent) | Medium |
| 65-73 | Continue passaging cells and freezing 2/3 when passage (passage by Gentle Cell Dissociation Reagent) | |
| 76 | Change medium to VG2i | VG2i |

TABLE 3

Comparison of components of mTeSR and E7 media.

| Component | mTeSR | E7 |
|---|---|---|
| DMEM/F-12 | + | + |
| L-Ascorbic Acid | + | + |
| Insulin | + | + |
| Transferrin | + | + |
| Selenium | + | + |
| FGF2 | + | + |
| TGFβ1 | + | |
| Glutathione | + | |
| L-Glutamine | + | |
| Defined Lipids | + | |
| Thiamine | + | |
| Trace Elements B | + | |
| Trace Elements C | + | |
| B-Mercaptoethanol | + | |
| Albumin (BSA) | + | |
| Pipecolic Acid | + | |
| LiCl | + | |
| GABA | + | |

Example 2. LTVEC Targeting in Human iPS Cells

This example describes the use of LTVEC targeting in human iPS cells. As shown in FIG. 1, we introduced by electroporation into human iPS cells propagated in VG2i medium the following nucleic acid molecules: (1) an LTVEC (0.67 μg); (2) a plasmid encoding a Cas9 endonuclease (5 μg); and (3) a plasmid encoding a CRISPR single guide RNA (gRNA) (10 μg). In one set of samples, the Cas9 and gRNA were excluded. Specifically, 3×10$^6$ cells were electroporated at a voltage of 700V, a capacitance of 25 uF, and a resistance of 400 ohms. The LTVEC comprised a 16.7 kb nucleic acid comprising mouse Adam6a and Adam6b genes flanked by homology arms containing 34 kb and 105 kb of genomic DNA derived from genomic regions that flank the 4.1 kb sequence of the human ADAM6 locus intended for deletion. The LTVEC also carried a drug selection cassette that directs the expression of an enzyme that imparts resistance to an antibiotic drug (hygromycin). The human ADAM6 gRNA used had the following sequence: GTATAGCCCTGTTACACATT (SEQ ID NO: 1).

Cells that took up the LTVEC and incorporated it into their genomes were able to grow and form colonies on a GELTREX™-coated tissue culture dish in a growth medium containing the antibiotic drug. Because we introduced 500 to 1,000 times more CRISPR/Cas9-encoding nucleic molecules than LTVEC molecules, most of the LTVEC-containing drug resistant colonies also contained, at least transiently, the CRISPR/Cas9 components. We picked drug resistant colonies and screened them by the loss-of-allele method (Valenzuela et al. (2003) *Nat. Biotech.* 21:652-660; Frendewey et al. (2010) *Methods Enzymol.* 476:295-307; incorporated herein by reference in their entireties) to identify clones that had the correctly targeted allele.

The results of the CRISPR/Cas9-assisted LTVEC targeting of the ADAM6 locus are shown in Table 4.

TABLE 4

CRISPR/Cas9-assisted LTVEC targeting.

| Targeting Condition | Targeting Efficiency |
|---|---|
| LTVEC Only | 3.1% |
| LTVEC + CRISPR | 7.3% |

When the LTVEC alone was introduced into human iPS cells, a targeting efficiency of 3.1% was observed. In contrast, combining the LTVEC with Cas9 guided by the ADAM6 gRNA resulted in a targeting efficiency of 7.3%.

Example 3. Effect of Low Osmolality Medium on Human iPS Cell Morphology

This example describes the effect of salt concentration, ionic strength, and/or osmolality on the pluripotency state of human iPS cells in culture. Human iPS cells were cultured on a MATRIGEL™ or GELTREX™ substrate in a medium described in Table 5 (final hLIF concentration of 100 U/mL; final CHIR99021 concentration of 3 μM, and final PD0325901 concentration of 0.5 μM) or in mTeSR™-hLIF medium.

TABLE 5

Medium for iPS cell culture.

| Component | Amount (v/v) |
|---|---|
| Base Medium | 24.75 |
| F-12 Medium | 24.75 |
| N2 ® Supplement | 0.5 |
| Neurobasal ® Medium | 49 |
| B-27 ® Supplement | 1 |
| Penicillin/Streptomycin | 1 |
| L-Glutamine (200 mM) | 1 |
| 2-Mercaptoethanol (55 mM) | 0.1836 |
| hLIF (1 × 10$^4$ units/mL) | 0.001 |

TABLE 5-continued

Medium for iPS cell culture.

| Component | Amount (v/v) |
|---|---|
| CHIR99021 (10 mM) | 0.03 |
| PD0325901 (10 mM) | 0.005 |

TABLE 6

Osmolality of medium and medium components.

| Medium or Medium Component | Osmolality (mOsm/kg) |
|---|---|
| 2i Medium | 261 |
| VG2i Medium | 233 |
| Neurobasal | 216 |
| DMEM/F-12 | 305 |
| DMEM | 340 |
| F-12 | 290 |
| VG-DMEM | 200 |

When the base medium used was DMEM, this medium was referred to as 2i medium. When the base medium used was VG-DMEM, this low osmolality medium was referred to as VG2i medium. The osmolality of VG2i medium (233 mOsm/kg) is lower than the osmolality of traditional 2i medium (261 mOsm/kg). Table 6 shows the osmolalities for these media as well as the osmolality of different base media and media components.

As shown in FIG. 2, human iPS cells cultured on MATRIGEL™ in 2i medium for a period of 8 days (FIG. 2A) or 12 days (FIG. 2B) displayed a morphology characteristic of iPS cells in a primed state, particularly growth in an epithelial monolayer and the appearance of apico-basal polarity.

mTeSR™-hLIF medium and VG2i medium were further evaluated for their effects on the morphology and pluripotency state of human iPS cells. In this study, human iPS cells were cultured on MATRIGEL™ or NuFF feeder cells in mTeSR™-hLIF medium (FIGS. 3A and 3C) or in VG2i medium (FIGS. 3B and 3D) for a period of 6 days. When cultured in mTeSR™-hLIF medium on MATRIGEL™ or NuFF feeder cells, human iPS cells displayed a morphology characteristic of a primed pluripotency state, particularly growth in an epithelial monolayer and the appearance of apico-basal polarity. Some cells cultured in mTeSR™-hLIF medium began to display a morphology characterized by three-dimensional clumping. By contrast, when cultured in VG2i medium on MATRIGEL™ or NuFF feeder cells, the human iPS cells displayed a morphology characteristic of a naïve pluripotency state, particularly growth in round, dome-shaped colonies and a lack of apico-basal polarity.

Figure 4A:
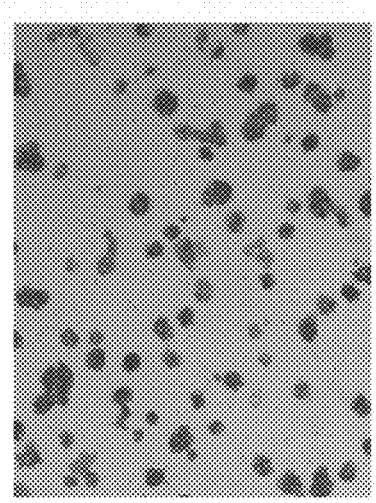
FIG. 4A depicts reprogrammed human iPS cells cultured in VG2i medium that have been stained for alkaline phosphatase.
Figure 4B:
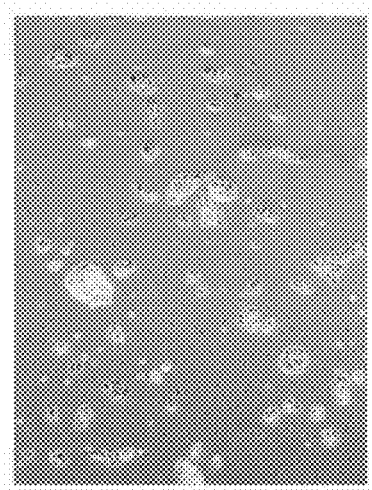
FIGS. 4B and 4C depict reprogrammed human iPS cells cultured in VG2i medium that have been immunostained for the expression of NANOG.
Figure 4C:
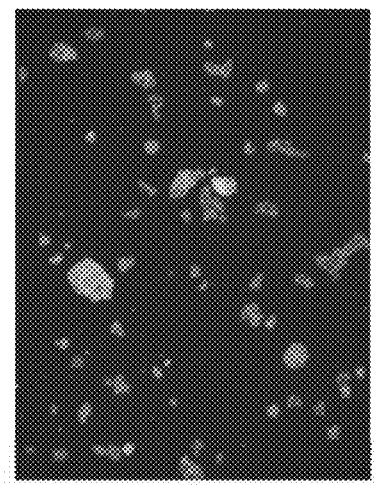

Example 4. Effect of Low Osmolality Medium on the Expression of Pluripotency Markers in Human iPS Cells This example describes the effect of salt concentration, ionic strength, and/or osmolality on the expression of pluripotency markers in human iPS cells that have been reprogrammed from a primed state to a naïve state. Following 24 days of culture in VG2i medium on a MATRIGEL™ substrate, reprogrammed naïve human iPS cells were stained for the expression of alkaline phosphatase or NANOG. It was observed that the reprogrammed cells strongly expressed both alkaline phosphatase (FIG. 4A) and NANOG (FIGS. 4B and 4C), which are indicative of a naïve pluripotency state.

Figure 6A:
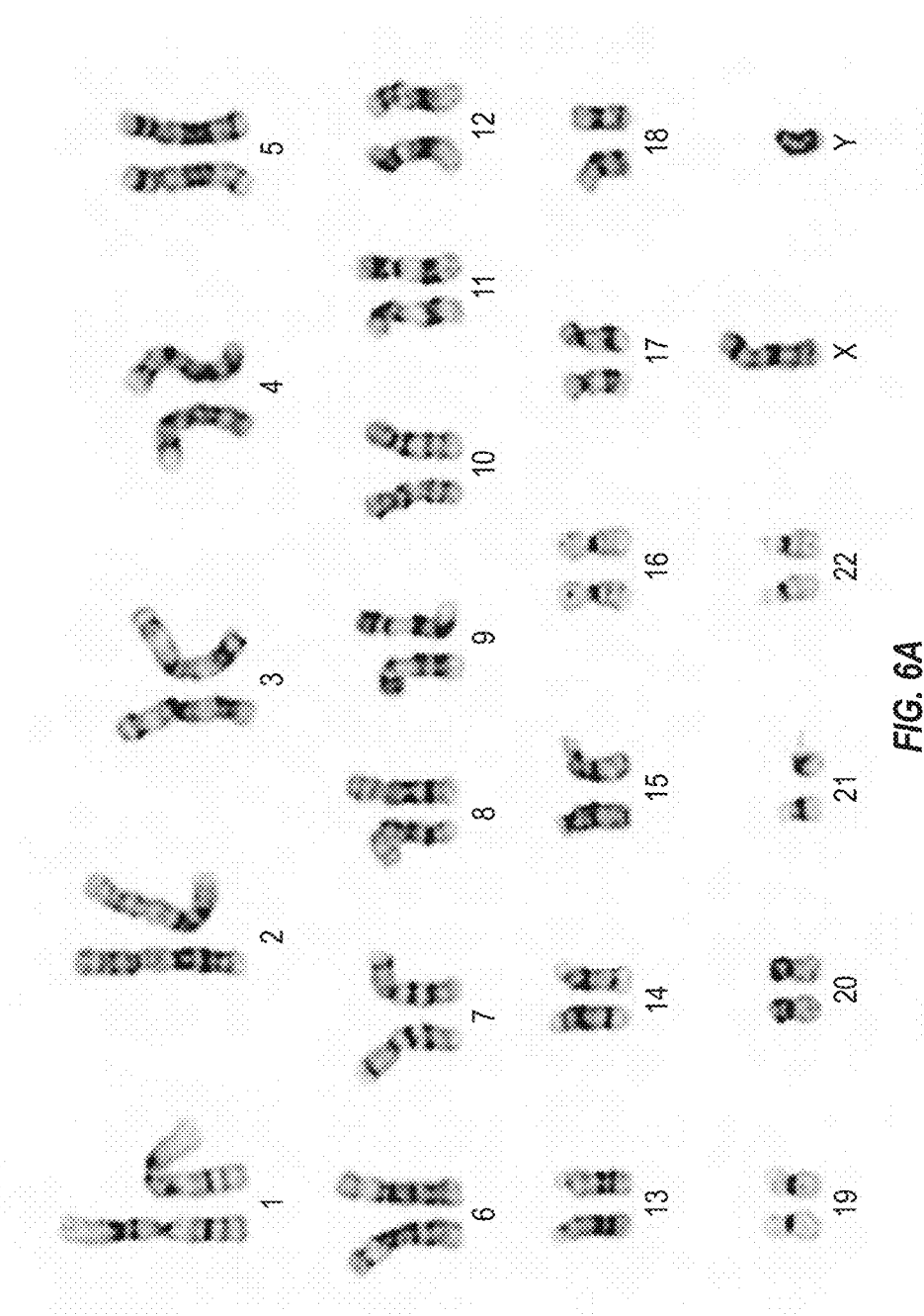
FIGS. 6A and 6B depict the karyotypes of cells from two different human iPS cell clones at passage 10 following dissociation with trypsin to create a single-cell suspension.
Figure 6B:
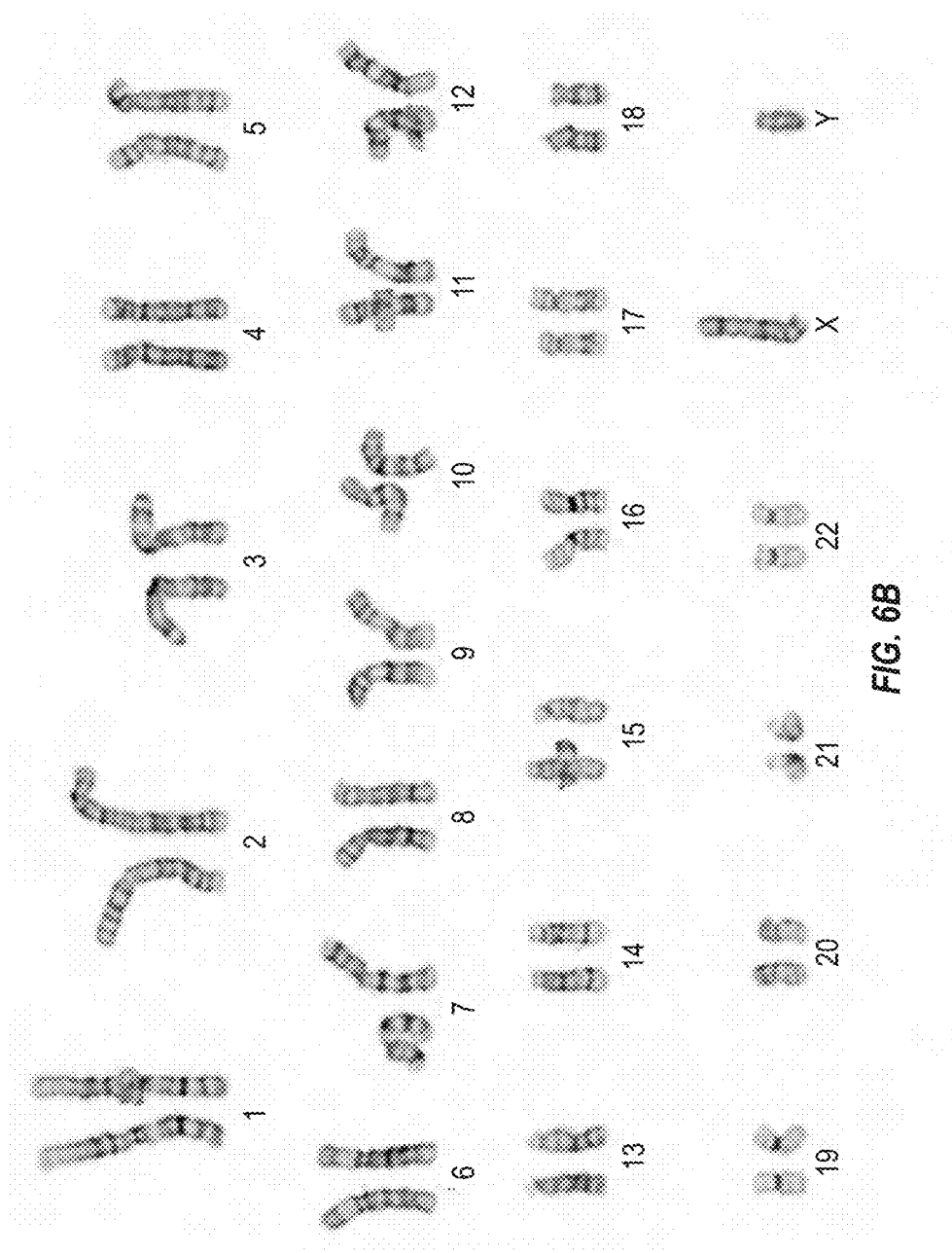

Example 5. Effect of Low Osmolality Medium on Enzymatic Dissociation and Subculture of Human iPS Cells In this example, human iPS cells that were reprogrammed to a naïve state using low osmolality VG2i medium were enzymatically dissociated using trypsin to create a single cell suspension (FIG. 5A). The cell suspension was passaged onto new GELTREX™-coated plates for subculture in VG2i medium. It was observed after 1 day (FIG. 5B) and 4 days (FIG. 5C) that the subcultured cells continued to display a morphology characteristic of cells in a naïve pluripotency state. Particularly, the cells grew as rounded dome-shaped colonies and did not exhibit an apico-basal polarity. It was notable that enzymatic dissociation could be performed in the absence of a ROCK inhibitor, which is typically necessary to prevent activation of pro-apoptotic pathways. This suggests that pro-apoptotic pathways are not as strongly activated during enzymatic dissociation and subculture in naïve human iPS cells cultured under the conditions identified herein. In addition, human iPS cells cultured in VG2i and passaged as single cells following enzymatic dissociation with trypsin maintain a normal karyotype. Two passage 10 human iPS cells derived from different clones and produced following dissociation with trypsin to create a single-cell suspension were karyotyped, and both had a normal 46 XY karyotype (FIGS. 6A and 6B).

wherein the low osmolality medium has an osmolality of about 200 mOsm/kg to about 250 mOsm/kg.

2. The in vitro culture of claim 1, wherein the hiPSCs:
   (a) express one or more pluripotency markers;
   (b) can differentiate into cells of any one of the endoderm, ectoderm, or mesoderm germ layers;
   (c) have a doubling time of between about 16 hours and about 24 hours; or
   (d) any combination of (a) to (c).

3. The in vitro culture of claim 1, wherein the hiPSCs have a normal karyotype.

4. The in vitro culture of claim 2, wherein the hiPSCs express the one or more pluripotency markers, and wherein the pluripotency markers comprise NANOG, alkaline phosphatase, or a combination thereof.

5. The in vitro culture of claim 1, wherein the hiPSCs are derived from non-pluripotent cells transformed to express a pluripotent state.

6. The in vitro culture of claim 5, wherein the transformed cells express reprogramming genes comprising Oct4, Sox2, Klf4, Myc, or any combination thereof.

7. The in vitro culture of claim 5, wherein the transformed cells are first cultured in a high osmolality medium prior to culturing in the low osmolality medium, wherein the high osmolality medium comprises bFGF.

8. The in vitro culture of claim 7, wherein the high osmolality medium has an osmolality of at least 290 mOsm/kg.

That which is claimed:

1. An in vitro culture comprising:
   (a) a population of nave human induced pluripotent stem cells (hiPSCs) that display a morphology characterized by compact, dome-shaped colonies; and
   (b) a low osmolality medium comprising a base medium and supplements, wherein the low osmolality medium comprises:
      (i) a leukemia inhibitory factor (LIF) polypeptide;
      (ii) a glycogen synthase kinase 3 (GSK3) inhibitor; and
      (iii) a MEK inhibitor;

9. The in vitro culture of claim 7, wherein:
   (a) the transformed cells are first cultured in the high osmolality medium until they express characteristics of a nave state;
   (b) the transformed cells are first cultured in the high osmolality medium for a period of about two months;
   (c) the transformed cells are first cultured in the high osmolality medium until they display a morphology characterized by three-dimensional cell clumps; or
   (d) a combination thereof.

10. The in vitro culture of claim 1, wherein the base medium comprises NaCl at about 3 mg/mL, sodium bicarbonate at about 2.2 mg/mL, and has an osmolality of about 200 mOsm/kg.

11. The in vitro culture of claim 1, wherein the base medium comprises glucose at about 4.5 mg/mL.

12. The in vitro culture of claim 1, wherein the base medium has an osmolality of about 180 mOsm/kg to about 250 mOsm/kg.

13. The in vitro culture of claim 12, wherein the low osmolality medium has an osmolality of about 233 mOsm/kg.

14. The in vitro culture of claim 1, wherein:
(a) the supplements comprise:
  (i) F-12 medium;
  (ii) N2 supplement;
  (iii) B-27 supplement;
  (iv) L-glutamine;
  (v) 2-mercaptoethanol; or
  (vi) any combination of (i) to (v);
(b) the LIF polypeptide is a human LIF (hLIF) polypeptide;
(c) the GSK3 inhibitor is CHIR99021;
(d) the MEK inhibitor is PD0325901; or
(e) any combination of (a) to (d).

15. The in vitro culture of claim 1, wherein the low osmolality medium comprises inhibitors consisting essentially of the glycogen synthase kinase 3 (GSK3) inhibitor and the MEK inhibitor.

16. The in vitro culture of claim 1, wherein the low osmolality medium comprises the base medium at about 24.75% (v/v), F-12 medium at about 24.75% (v/v), N2 supplement at about 0.5% (v/v), B-27 supplement at about 1% (v/v), L-glutamine at about 2 mM, 2-mercaptoethanol at about 0.1 mM, hLIF at about 100 units/mL, CHIR99021 at about 3 µM, and PD0325901 at about 0.5 µM.

17. The in vitro culture of claim 1, wherein the low osmolality medium does not comprise one or more of the following: bFGF supplement; TGF-β1 supplement; JNK inhibitor; p38 inhibitor; ROCK inhibitor; and PKC inhibitor.

18. The in vitro culture of claim 1, wherein the hiPSCs are cultured on newborn human foreskin fibroblast (NuFF) feeder cells.

19. The in vitro culture of claim 1, wherein the hiPSCs are in a single-cell suspension.

20. The in vitro culture of claim 19, wherein the hiPSCs in the single-cell suspension:
(a) maintain expression of one or more pluripotency markers;
(b) maintain a naïve state; or
(c) a combination thereof.

21. The in vitro culture of claim 19, wherein the hiPSCs in the single-cell suspension maintain a normal karyotype.

22. The in vitro culture of claim 12, wherein the low osmolality medium further comprises F-12 medium.

23. The in vitro culture of claim 17, wherein the low osmolality medium does not comprise bFGF supplement.

* * * * *

UNITED STATES PATENT AND TRADEMARK OFFICE
CERTIFICATE OF CORRECTION

PATENT NO.         : 10,428,310 B2
APPLICATION NO.    : 14/884293
DATED              : October 1, 2019
INVENTOR(S)        : Junko Kuno et al.

Page 1 of 1

It is certified that error appears in the above-identified patent and that said Letters Patent is hereby corrected as shown below:

In the Claims

Claim 1, Column 53, Line 59:
Delete "nave" and insert --naïve--

Claim 9, Column 54, Line 60:
Delete "nave" and insert --naïve--

Signed and Sealed this
Twenty-sixth Day of November, 2019

Andrei Iancu
*Director of the United States Patent and Trademark Office*

```
                        SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthesized

<400> SEQUENCE: 1
gtatagccct gttacacatt                                                   20

<210> SEQ ID NO 2
<211> LENGTH: 23
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (2)...(21)
<223> OTHER INFORMATION: n = A,T,C or G

<400> SEQUENCE: 2
gnnnnnnnnn nnnnnnnnnn ngg                                               23
```